(12) United States Patent
Weglicki et al.

(10) Patent No.: US 9,474,761 B2
(45) Date of Patent: Oct. 25, 2016

(54) USE OF NK-1 RECEPTOR ANTAGONISTS FOR TREATING HYPOMAGNESEMIA, NEUROGENIC INFLAMMATION, AND CARDIAC DYSFUNCTION ASSOCIATED WITH EGFR-BLOCKING DRUGS

(71) Applicants: William B. Weglicki, Potomac, MD (US); Iu Tong Mak, Gaithersburg, MD (US)

(72) Inventors: William B. Weglicki, Potomac, MD (US); Iu Tong Mak, Gaithersburg, MD (US)

(73) Assignee: THE GEORGE WASHINGTON UNIVERSITY, Washington, DC (US)

( * ) Notice: Subject to any disclaimer, the term of this patent is extended or adjusted under 35 U.S.C. 154(b) by 0 days.

(21) Appl. No.: 14/735,396

(22) Filed: Jun. 10, 2015

(65) Prior Publication Data

US 2015/0352120 A1 Dec. 10, 2015

Related U.S. Application Data

(60) Provisional application No. 62/010,198, filed on Jun. 10, 2014.

(51) Int. Cl.
| | |
|---|---|
| *A61K 31/5377* | (2006.01) |
| *A61K 31/444* | (2006.01) |
| *A61K 31/495* | (2006.01) |
| *A61K 31/4035* | (2006.01) |
| *A61K 31/4985* | (2006.01) |

(52) U.S. Cl.
CPC ....... *A61K 31/5377* (2013.01); *A61K 31/4035* (2013.01); *A61K 31/444* (2013.01); *A61K 31/495* (2013.01); *A61K 31/4985* (2013.01)

(58) Field of Classification Search
None
See application file for complete search history.

(56) References Cited

PUBLICATIONS

Santini et al., Lancet Oncology (2012), 13(10), pp. 1020-1024.*
Altura et al., "Comparative effects of a Mg-enriched diet and different orally administered magnesium oxide preparations on ionized Mg, Mg metabolism and electrolytes in serum of human volunteers." Journal of the American College of Nutrition, 1994; 13(5): 447-454.
Barbagallo et al., "Magnesium homeostasis and aging." Magnesium Research, 2009; 22(4): 235-246.
Cao et al., "Methionine sulfoxide reductase B1 (MsrB1) recovers TRPM6 channel activity during oxidative stress." Journal of Biological Chemistry, Aug. 20, 2010; 285(34):26081-7.
Chen et al., "Mechanisms of cardiac dysfunction associated with tyrosine kinase inhibitor cancer therapeutics." Circulation, 2008; 117: 84-95.
Dehlin et al., "Substance P acting via the neurokinin-1 receptor regulates adverse myocardial remodeling in a rat model of hypertension." International Journal of Cardiology, 2013 12; 168(5):4643-51.
Dimke et al., "Effects of the EGFR Inhibitor Erlotinib on Magnesium Handling." Journal of the American Society of Nephrology, Aug. 2010; 21(8):1309-16. doi: 10.1681/ASN.2009111153. Epub Jul. 1, 2010.
Doherty et al., "Multi-parameter in vitro toxicity testing of crizotinib, sunitinib, erlotinib, and nilotinib in human cardiomyocytes." Toxicology and Applied Pharmacology, Oct. 1, 2013; 272(1):245-55. doi:10.1016/j.taap.2013.04.027. Epub May 21, 2013.
Fletcher et al., "EGFR inhibition induces proinflammatory cytokines via NOX4 in HNSCC." Molecular Cancer Research, Dec. 2013; 11(12):1574-84. doi: 10.1158/1541-7786.MCR-13/0187. Epub Sep. 18, 2013.
Garrett et al., "Cetuximab in the treatment of patients with colorectal cancer." Expert Opinion on Biological Therapy, 2011; 11: 937-949.
Gill et al., "NADPH oxidases in the kidney." Antioxidants and Redox Signaling, 2006; 8:1597-1607; 23.
Groenestege et al., "Impaired basolateral sorting of pro-EGF causes isolated recessive renal hypomagnesemia." Journal of Clinical Investigation, 2007; 117: 2260-2267.
Hahn et al., "Cancer therapy-induced cardiotoxicity: basic mechanisms and potential cardioprotective therapies." Journal of the American Heart Association, Apr. 22, 2014;3(2):e000665. doi:10.1161/JAHA.113.000665.
Hasinoff, B.B., "The cardiotoxicity and myocyte damage caused by small molecule anticancer tyrosine kinase inhibitors is correlated with lack of target specificity." Toxicology and Applied Pharmacology, 2010; 244(2): 190-195.
Ho et al., "Human monocytes and macrophages express substance P and neurokinin-1 receptor." Journal of Immunology, 1997; 159:5654-5660.
Imai et al., "Comparing antibody and small-molecule therapies for cancer." Nature Reviews. Cancer. Sep. 2006;6(9):714-27. Review.
International Cosmetic Ingredient Dictionary and Handbook, eds. Wenninger and McEwen, pp. 1656-1661, 1626, 1654-1655, 1673-1686 and 1693-1697 (The Cosmetic, Toiletry, and Fragrance Assoc., Washington, D.C., 7th Edition, 1997).
Janjigian et al., "Phase I/II trial of cetuximab and erlotinib in patients with lung adenocarcinoma and acquired resistance to erlotinib." Clinical Cancer Research, Apr. 15, 2011;17(8):2521-7. Epub Jan. 19, 2011.
Kramer et al., "Dietary Mg-intake influence circulating pro-inflammatory neuropeptide levels and loss of myocardial tolerance to postischemic stress." Experimental Biology and Medicine, 2003; 228:665-673.

(Continued)

*Primary Examiner* — Brian J Davis
(74) *Attorney, Agent, or Firm* — Cooley LLP

(57) ABSTRACT

The present disclosure provides methods for alleviating or preventing the negative physiological side effects associated with the administration of EGFR blocking therapeutics. The disclosure provides, inter alia, methods for treating or preventing: hypomagnesemia, cardiac dysfunction, and skin lesions, which are induced by EGFR blocking drugs, by administering an NK-1 receptor antagonist.

25 Claims, 10 Drawing Sheets

(56) References Cited

PUBLICATIONS

Kramer et al., "Neurogenic inflammation and cardiac dysfunction due to hypomagnesemia " American Journal of the Medical Sciences, 2009; 338(1):22-27.

Ledeganck et al., "The TRPM6/EGF pathway is downregulated in a rat model of cisplatin nephrotoxicity." PLoS One, 2013;8(2):e57016. doi: 10.1371/journal.pone.0057016. Epub Feb. 15, 2013.

Lockhart et al., "The epidermal growth factor receptor as a target for colorectal cancer therapy." Seminars in Oncology, 2005; 32: 52-60.

Mak et al., "Loss of neutral Endopeptidase activity contributes to neutrophil activation and cardiac dysfunction during chronic hypomagnesemia. Protection by substance P receptor blockade." Experimental and Clinical Cardiology, 2011;16(4):121-124.

Mak et al., "EGFR-TKI, erlotinib, causes hypomagnesemia, oxidative stress, and cardiac dysfunction: attenuation by NK-1 receptor blockade." Journal of Cardiovascular Pharmacology, Jan. 2015; 65(1):54-61.

Mak et al., "Suppression of neutrophil and endothelial activation by substance P receptor blockade in the Mg-deficient rat." Magnesium Research, 2003; 16(2):91-97.

Mak, et al., "Mg supplementation Attenuates Ritonavir-induced Hyperlipidemia, Oxidative Stress and Cardiac Dysfunction in Rats." American Journal of Physiology: Regulatory, Integrative and Comparative Physiology, 2013; 305: R1102-R1111.

Mak, et al., "AZT-Induced cardiovascular toxicity—attenuation by Mg-supplementation." Cardiovascular Toxicology, 2009; 9(2):78-85.

McCutcheon's Detergents and Emulsifiers, North American Edition, pp. 317-324 (1986).

Metro, et al., "Epidermal growth factor receptor (EGFR) targeted therapies in non-small cell lung cancer (NSCLC)." Rev Recent Clin Trials. Jan. 2006;1(1):1-13.

Nistala et al., "Redox control of renal function and hypertension." Antioxidants and Redox Signaling, Dec. 2008;10(12):2047-89. doi: 10.1089/ars.2008.2034.

Orcutt, et al., "Erlotinib-mediated inhibition of EGFR signaling induces metabolic oxidative stress through NOX4." Cancer Research, Jun. 1, 2011;71(11):3932-40.

Petrelli, et al., "Risk of anti-EGFR monoclonal antibody-related hypomagnesemia: systematic review and pooled analysis of randomized studies." Expert Opinion on Drug Safety May 2012, vol. 11, No. 51, pp. S9-S19.

Sagarin, Cosmetics, Science and Technology, 2nd Edition, vol. 1, pp. 32-43 (1972).

Saif M.W., "Management of hypomagnesemia in cancer patients receiving chemotherapy." Journal of Supportive Oncology, May-Jun. 2008;6(5):243-8.

Sawyers C., "Targeted cancer therapy." Nature, 432: 294-297, 2004.

Schettino et al. "Erlotinib: an EGF receptor tyrosine kinase inhibitor in non-small-cell lung cancer treatment." Expert Review of Respiratory Medicine, Apr. 2008;2(2):167-78. doi:10.1586/17476348.2.2.167.

Tejpar et al., "Magnesium wasting associated with epidermal-growth-factor receptor-targeting antibodies in colorectal cancer: a prospective study." The Lancet. Oncology, 2007, 8: 387-394.

Thebault S et al., "EGF increases TRPM6 activity and surface expression." Journal of the American Society of Nephrology, Jan. 2009;20(1):78-85. Epub Dec. 10, 2008.

Van Angelen et al., "Cisplatin-induced injury of the renal distal convoluted tubule is associated with hypomagnesaemia in mice." Nephrology Dialysis Transplant, 2013; 28:879-89.

Vickers et al., "Association of hypomagnesemia with inferior survival in a phase III, randomized study of cetuximab plus best supportive care versus best supportive care alone: NCIC CTG/AGITG CO.17." Annals of Oncology, Apr. 2013; 24(4):953-60.

Weglicki WB, et al., "Neutral endopeptidase inhibition enhances substance P mediated inflammation due to hypomagnesemia " Magnesium Research, 2009; 22:1-7.

Weglicki et al., "Pathobiology of magnesium deficiency: A cytokine/neurogenic inflammation hypothesis." American Journal of Physiology, 1992; 263: R734-R737.

Weglicki et al., "The EGFR tyrosine kinase inhibitor tyrphostin AG-1478 causes hypomagnesemia and cardiac dysfunction." Canadian Journal of Physiology of Pharmacology, 2012; 90(8):1145-9.

Weglicki et al., "The role of Magnesium Deficiency in Cardiovascular and Intestinal Inflammation." Magnesium Research, 2012; 23(4): S199-206.

Weglicki et al., "Role of free radicals and substance P in magnesium deficiency." Cardiovascular Research, 1996;31:677-682.

Yang B et al., "Tyrosine kinase inhibitor (TKI)-induced cardiotoxicity: approaches to narrow the gaps between preclinical safety evaluation and clinical outcome." Journal of Applied Toxicology, Dec. 2012; 32(12):945-51. doi: 10.1002/jat.2813. Epub Sep. 10, 2012.

Vincenzi et al., "Aprepitant for Erlotinib-Induced Pruritus," New England Journal of Medicine, Jul. 22, 2010; 363(4): 397-398.

Bryant Furlow; "Hypomagnesemia is Associated with Inferior Survival in Patients Receiving Cetuximab for Advanced Colorectal Cancer," Nov. 13, 2012; retrieved from http://www.cancertherapyadvisor.com/gastrointestinal-cancers/hypomagnesemia-is-associated-with-inferior-survival-in-patients-receiving-cetuximab-for-advanced-colorectal-cancer/article/268069/.

\* cited by examiner

USE OF NK-1 RECEPTOR ANTAGONISTS FOR TREATING HYPOMAGNESEMIA, NEUROGENIC INFLAMMATION, AND CARDIAC DYSFUNCTION ASSOCIATED WITH EGFR-BLOCKING DRUGS

CROSS REFERENCE TO RELATED APPLICATIONS

The present application claims the benefit of priority to U.S. Provisional Application No. 62/010,198, filed on Jun. 10, 2014, the contents of which are hereby incorporated by reference in their entirety.

STATEMENT REGARDING FEDERALLY SPONSORED RESEARCH OR DEVELOPMENT

This disclosure was made with Government support under contract R21-HL108311 awarded by the NIH. The U.S. Government has certain rights in the disclosure.

FIELD OF THE DISCLOSURE

The present disclosure relates to methods and compositions for treating magnesium deficiency and other side effects induced by administration of chemotherapeutic agents. More particularly, the disclosure relates to compositions and methods that are useful for treating hypomagnesemia, cardiac dysfunction, and neurogenic inflammation associated with epidermal growth factor receptor (EGFR) blocking drugs.

BACKGROUND

Therapies targeted to inhibit the activity of the EGF pathway through its receptor (EGFR) have seen increased application in anti-cancer therapy (Sawyers C., Nature 432: 294-297, 2004). The EGF pathway can be inhibited by injections of monoclonal antibodies (antibody inhibitors) targeting an extracellular epitope of the EGFR, or by chemical agents (small molecule inhibitors) that inhibit the receptor tyrosine kinase on the cytoplasmic side of cancer cells (Sawyers, 2004; Imai and Takaoka, Nat Rev Cancer. 2006 September; 6(9):714-27).

Erlotinib (Tarceva®) is approved as a first-line and maintenance treatment, and 2nd or 3rd-line treatment for advanced-stage non-small cell lung cancer. It is an orally administered reversible EGFR tyrosine kinase inhibitor (TKI) targeting the EGF receptor, which is up-regulated in the majority of lung, colorectal, and head and neck cancers (Schettino et al., 2008 April; 2(2):167-78).

These anti-cancer therapies, such as Erlotinib, have demonstrated success and are a welcomed addition to the fight against cancer. However, there are also significant drawbacks associated with the utilization of the aforementioned EGFR receptor antagonists. These drawbacks, which will be elaborated upon below, decrease patient compliance with the therapeutic and also limit the patient populations that can be effectively treated by the EGFR antagonistic compounds.

For example, EGFR activation is required for active epithelial Mg-absorption/reabsorption that is mediated by the transient receptor potential cation channel, subfamily M, member 6 (TRPM6) channel in the kidney and colon (Tejpar et al., Lancet Oncol. 2007, 8: 387-394). Treatment of patients with monoclonal antibodies (cetuximab and panitumumab) targeting the EGFR in colorectal cancer were found to cause pronounced hypomagnesemia (Tejpar et al., 2007; Petrelli et al., Expert Opinion on Drug Safety, May 2012, Vol. 11, No. 51, Pages S9-S19). Noticeable hypomagnesemia was also observed in patient receiving cetuximab plus erlotinib (Janjigian et al., Clin Cancer Res. 2011 Apr. 15; 17(8):2521-7). The association of hypomagnesemia with EGFR antagonistic compounds is troublesome and represents a serious drawback for utilizing these compounds as anti-malignant agents.

Further, Erlotinib can provoke cellular oxidative stress in cancer cells through NOX-4 up-regulation (Fletcher et al., Mol Cancer Res., 2013 December; 11(12):1574-84, Epub 2013 Sep. 18; Orcutt et al., Cancer Res. 2011 Jun. 1; 71(11):3932-40, Epub 2011 Apr. 11). Previous work has shown that an experimental TKI, tyrphostin AG 1478, which is chemically similar to erlotinib, displayed substantial cardiac dysfunctional effects, that were associated with enhanced neurogenic inflammation (elevated circulating levels of substance P (SP)), oxidative stress, and hypomagnesemia (Weglicki et al., Can. J. Physiol. Pharmacol. 2012; 90(8):1145-9).

The present disclosure shows that chronic treatment of rats with an EGFR blocking drug, such as erlotinib, induces significant: hypomagnesemia, systemic oxidative stress, cardiac dysfunction, and skin lesions and rashes. Thus, the present disclosure not only supports some of the previous findings regarding negative effects associated with utilization of EGFR blocking therapeutics, but it also elucidates further insights into the potentially harmful side effects associated with such.

Consequently, there is a great need in the medical community for the development of novel therapeutic compounds, compositions, and methods of treatment, which help to alleviate the aforementioned deleterious side effects associated with administration of EGFR blocking agents in human patients.

SUMMARY OF THE DISCLOSURE

The present disclosure provides therapeutic compositions and methods of treatment, which effectively diminish, alleviate, or otherwise prevent, many of the negative physiological effects associated with the administration of EGFR antagonistic therapeutics.

In aspects, the disclosure provides that many of the aforementioned negative side effects induced by EGFR blocking drugs can be reduced or inhibited by administration of substance P antagonists or neurokinin-1 (NK-1) receptor antagonists.

In aspects, the present disclosure provides methods for treating or preventing hypomagnesemia, and other side effects such: as neurogenic inflammation, systemic oxidative stress, cardiac dysfunction, and skin lesions and rashes, which are induced by EGFR blocking drugs, said methods comprising, inter alia, administering an NK-1 receptor antagonist.

In one embodiment, the NK-1 receptor antagonist is aprepitant (Emend™). In one embodiment, the EGFR blocking drug is erlotinib.

Consequently, in some aspects, the present disclosure provides for an improved method of cancer treatment, which comprises administering an NK-1 receptor antagonist in conjunction with an EGFR blocking agent.

In some aspects, the disclosure provides a method for reducing the negative physiological side effects associated with treating cancer patients with an EGFR blocking agent.

In some embodiments, an NK-1 receptor antagonist is administered to a subject receiving an EGFR blocking drug who is in need of such treatment. In one embodiment, the subject receiving an EGFR blocking drug is in need of a treatment with an NK-1 receptor antagonist if the subject has serum Mg levels below certain threshold levels which are described in more detail below. In another embodiment, the subject receiving an EGFR blocking drug is in need of a treatment with an NK-1 receptor antagonist if the subject shows signs or symptoms of cardiac dysfunction, neurogenic inflammation, and/or skin lesions.

In various embodiments, the disclosure comprises administering about 20 to about 125 mg, about 50 to about 100 mg, or about 80 to about 125 mg of an NK-1 receptor antagonist daily to a subject receiving an EGFR blocking drug. In some embodiments, the subject receiving an EGFR blocking drug may be administered at least one loading dose of an NK-1 receptor antagonist followed by one or more maintenance doses. The NK-1 receptor antagonist may be administered about 1 week, 2 weeks, 3 weeks or 4 weeks after the first dose of an EGFR blocking drug.

The disclosure further provides topical compositions of an NK-1 receptor antagonist for treating skin changes induced by an EGFR blocking drug.

In one embodiment, the invention provides a method for treating or preventing hypomagnesemia in a subject receiving an epidermal growth factor receptor (EGFR) blocking drug, comprising administering to the subject an effective dose of a neurokinin-1 (NK-1) receptor antagonist. In various embodiments, the NK-1 receptor antagonist is selected from the group consisting of aprepitant, fosaprepitant, serlopitant, vestipitant, tradipitant, orvepitant, casopitant and a pharmaceutically acceptable salt thereof. In one embodiment, the NK-1 receptor antagonist is aprepitant.

In one embodiment, the effective dose of the NK-1 receptor antagonist is between about 1 to about 150 mg per day. In another embodiment, the effective dose of the NK-1 receptor antagonist is between about 20 to about 125 mg per day. In yet another embodiment, the effective dose of the NK-1 receptor antagonist is between about 50 to about 100 mg per day. In yet another embodiment, the effective dose of the NK-1 receptor antagonist is between about 80 to about 125 mg per day. In yet another embodiment, the effective dose of the NK-1 receptor antagonist is between about 120 to about 200 mg per day.

In one aspect of the invention, the NK-1 receptor antagonist is administered once daily. In another aspect of the invention, the NK-1 receptor antagonist is administered according to a schedule, said schedule comprising: a) first administering at least one loading dose; and b) second administering at least one maintenance dose. In various embodiments, the loading dose is about 1.5 times, 2 times, 3 times, 4 times or 5 times the maintenance dose. In one embodiment, the loading dose is about 125 mg and the maintenance dose is about 80 mg.

In one embodiment, the loading dose is administered on day 1 and the maintenance dose is administered on day 2 and thereafter. In another aspect, the maintenance dose is administered once a day, once every other day, once every third day, once every fourth day or once a week. In yet another aspect, the NK-1 receptor antagonist is administered according to a schedule, said schedule comprising administering a loading dose on day 1 and administering a maintenance dose every day for the next 6 days and repeating this schedule every week until required. In yet another aspect, the schedule for administering an NK-1 receptor antagonist comprises administering a loading dose on day 1 and administering a maintenance dose on days 2 and 3 and repeating this schedule every week until required.

In one embodiment, the NK-1 receptor antagonist is administered a week after the subject receives a first dose of the EGFR blocking drug. In one aspect of the invention, the EGFR blocking drug is a small molecule inhibitor or an antibody. In one embodiment, the small molecule inhibitor of EGFR is selected from the group consisting of erlotinib, gefitinib, afatinib, brigatinib, icotinib, lapatinib, and a pharmaceutically acceptable salt thereof. In one embodiment, the antibody inhibitor of EGFR is selected from cetuximab or panitumumab. In one embodiment, the EGFR blocking drug is erlotinib.

In one embodiment, the invention provides a method for treating or preventing hypomagnesemia in a subject receiving an epidermal growth factor receptor (EGFR) blocking drug, comprising administering to the subject an effective dose of a neurokinin-1 (NK-1) receptor antagonist, wherein the EGFR blocking drug is erlotinib and the NK-1 receptor antagonist is aprepitant.

In one embodiment, the subject receiving the EGFR blocking drug has a serum magnesium level of 1.2 mg/dl or lower. In another embodiment, the subject receiving the EGFR blocking drug has a Eastern Cooperative Oncology Group Performance Status (ECOG PS) Grade of 2 or higher. In yet another embodiment, the subject receiving the EGFR blocking drug has a serum magnesium level of 1.2 mg/dl or lower even after intravenous magnesium treatment. In yet another embodiment, the subject receiving the EGFR blocking drug has a serum magnesium level of 1.2 mg/dl or lower and shows side effects to intravenous magnesium treatment.

In one embodiment, the subject receiving the EGFR blocking drug subject is receiving two EGFR blocking drugs. In one aspect, one of the EGFR blocking drugs is an antibody and the second EGFR blocking drug is a small molecule inhibitor. In one embodiment, the EGFR blocking antibody is selected from cetuximab or panitumumab. In one embodiment, the small molecule inhibitor of EGFR is selected from the group consisting of erlotinib, gefitinib, afatinib, brigatinib, icotinib, lapatinib and a pharmaceutically acceptable salt thereof. In one embodiment, the subject is receiving cetuximab and erlotinib as EGFR blocking drugs.

In one embodiment, the invention provides a method for treating or preventing cardiac dysfunction in a subject receiving an epidermal growth factor receptor (EGFR) blocking drug, comprising administering to the subject an effective dose of a neurokinin-1 (NK-1) receptor antagonist. In another embodiment, the invention provides a method for treating or preventing neurogenic inflammation or systemic oxidative stress in a subject receiving an epidermal growth factor receptor (EGFR) blocking drug, comprising administering to the subject an effective dose of a neurokinin-1 (NK-1) receptor antagonist. In yet another embodiment, the invention provides a method for treating or preventing skin lesions in a subject receiving an epidermal growth factor receptor (EGFR) blocking drug, comprising administering to the subject an effective dose of a neurokinin-1 (NK-1) receptor antagonist.

In one embodiment, the invention provides a topical composition comprising a NK-1 receptor antagonist and a pharmaceutically acceptable carrier or excipient. In one aspect, the NK-1 receptor antagonist is aprepitant.

BRIEF DESCRIPTION OF THE DRAWINGS

FIG. 7A shows the effect on left ventricular ejection fraction (LVEF); FIG. 7B shows the effect on left ventricular percent fractional shortening (LV % FS); and FIG. 7C shows mitral valve E/A ratio.

FIG. 8A shows the effect on cardiac output (CO) and FIG. 8B shows the effect on aortic pressure maximum (Ao Pmax).

FIG. 9A shows the effect on interventricular septum dimension in diastole (IVSd) and FIG. 9B shows the effect on interventricular septum dimension in systole (IVSs).

FIG. 10A shows the effect on LV posterior wall thickness in diastole (LVPWd) and FIG. 10B shows the effect on LV posterior wall thickness in systole (LVPWs).

DETAILED DESCRIPTION

The epidermal growth factor receptor (EGFR) is a tyrosine kinase transmembrane receptor that is stimulated by ligands including amphiregulin, epiregulin and transforming growth factor-α, leading to homo- or heterodimerization with ErbBfamily members and subsequent signaling of the Ras-Raf-MAP, PI3K and Akt pathways (Garrett and Eng, Expert Opin Biol Ther 2011; 11: 937-949). These pathways are important for the regulation of cell proliferation and inhibition of apoptosis and can be activated in colorectal cancer (Lockhart and Berlin, Semin Oncol 2005; 32: 52-60). Other cancers driven by deregulated EGFR include non-small cell lung cancer (NSCLC), head and neck squamous cell carcinoma (HNSCC), malignant glioma, breast cancer, esophageal cancer, gastric cancer, renal cancer, cervical cancer, prostate cancer, ovarian cancer, pancreatic cancer, and hepatocellular cancer, including metastatic forms thereof.

Figure 1:
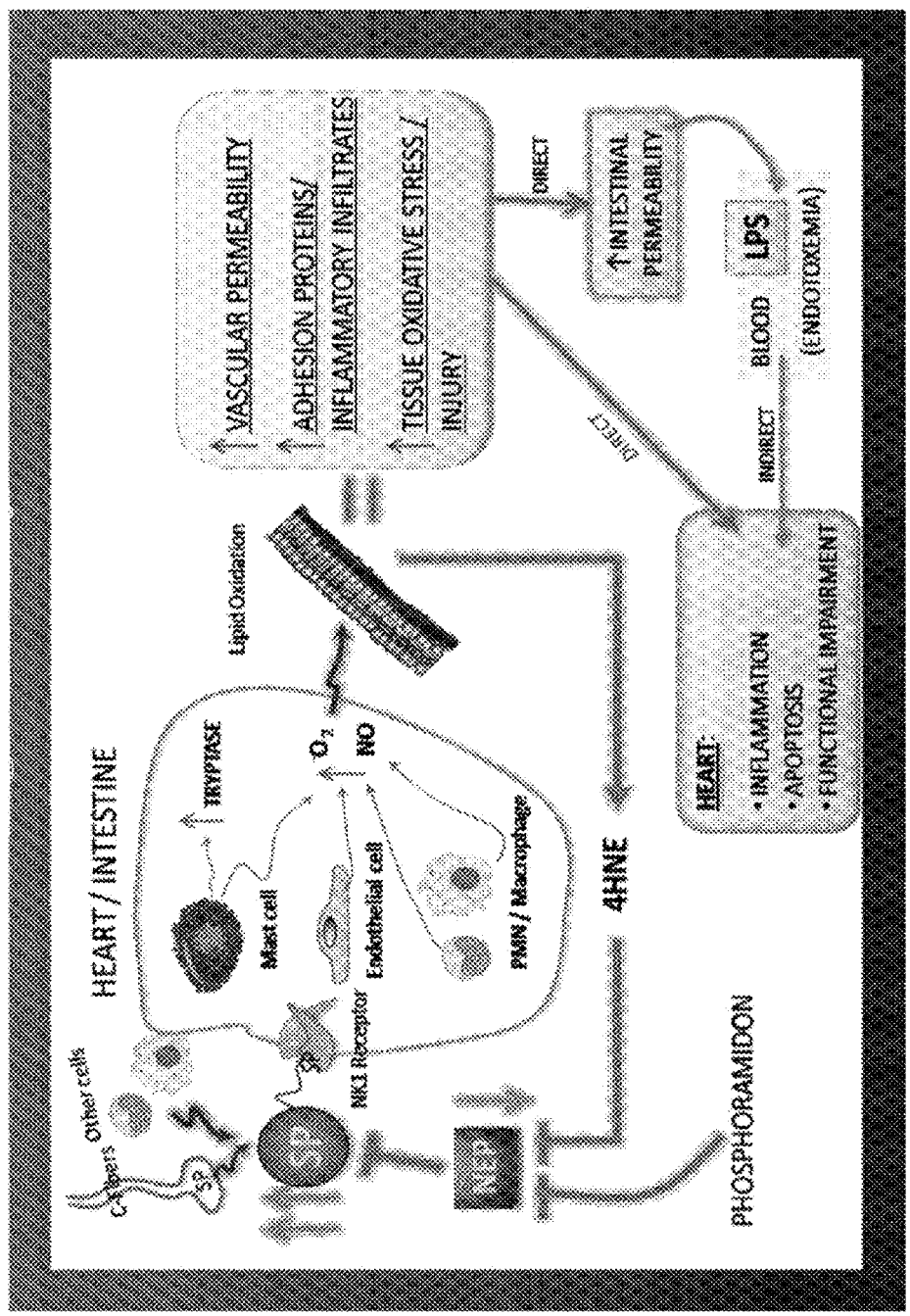
FIG. 1 shows the schematic for proposed mechanisms of cardiac/gut interactions in magnesium deficiency.
Figure 2:
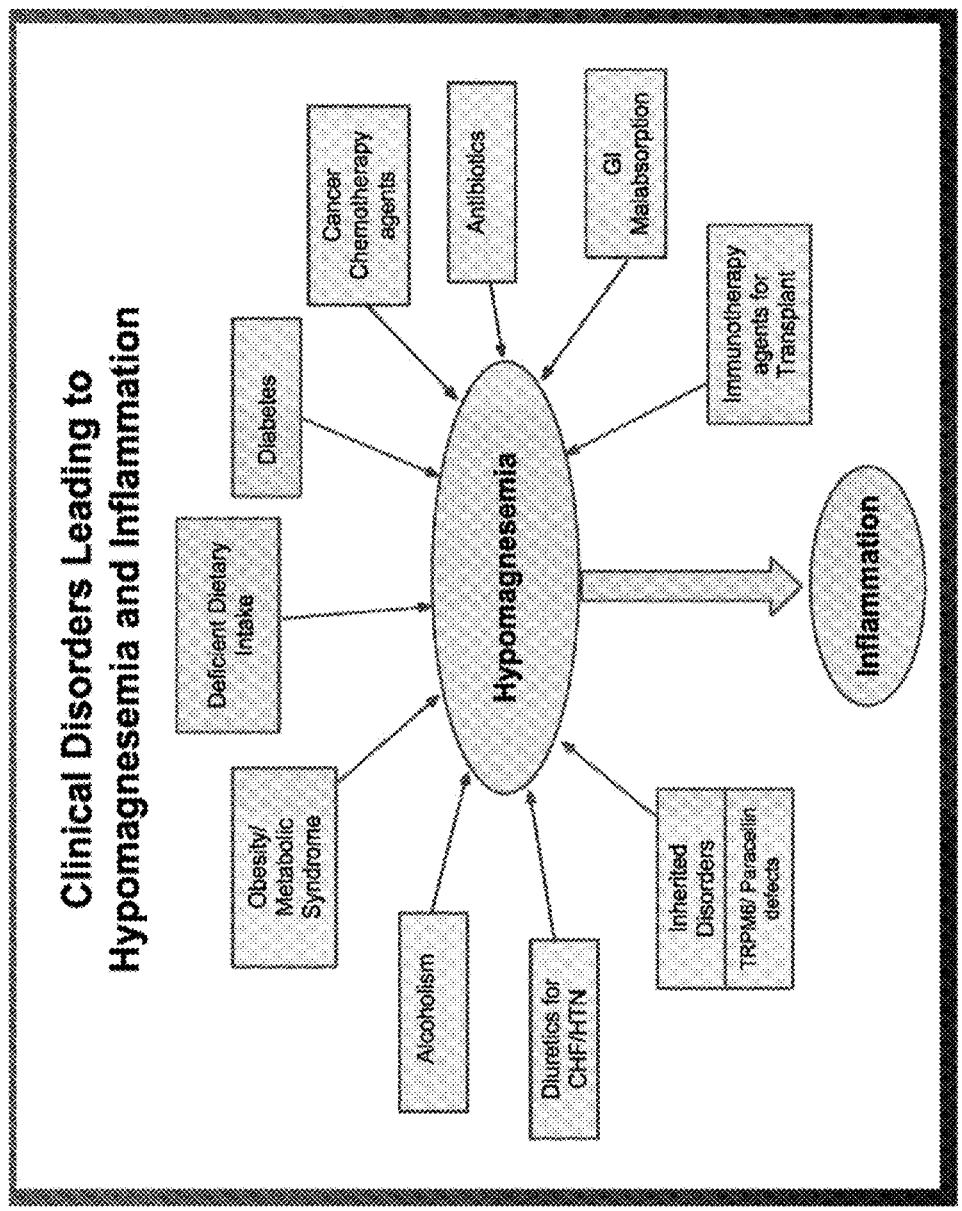
FIG. 2 shows the schematic for clinical disorders that may lead to hypomagnesemia and inflammation.

As discussed above, EGFR activation is required for active epithelial Mg-absorption/reabsorption that is mediated by the transient receptor potential cation channel, subfamily M, member 6 (TRPM6) channel in the kidney and colon (Tejpar et al., Lancet Oncol. 2007, 8: 387-394). Treatment of patients with EGFR inhibitors was found to cause pronounced hypomagnesemia. Hypomagnesemia can increase vascular permeability, lead to inflammation, and cause oxidative stress. These events can ultimately lead to cardiac dysfunction. See FIG. 1 for the schematic of the possible changes mediated by hypomagnesemia. FIG. 2 shows clinical disorders that may lead to hypomagnesemia and inflammation.

EGFR Blocking Drugs

An EGFR inhibitor can be a monoclonal antibody or a small molecule inhibitor. EGFR directed monoclonal antibodies in clinical use include cetuximab and panitumumab. Cetuximab is a humanized monoclonal antibody that binds to an extracellular epitope on EGFR and blocks activation of the receptor by preventing both ligand binding and receptor dimerization. Cetuximab in combination with chemotherapy has been approved by health authorities for the treatment of metastatic colorectal cancer and for the treatment of locally advanced and metastatic head and neck cancer. Panitumumab is a human IgG2 mAB against EGFR and approved for treatment of metastatic colorectal cancer. Other monoclonals in clinical development are zalutumumab, nimotuzumab, matuzumab and necitumumab.

Small molecule inhibitors that target EGFR include erlotinib and gefitinib, both binding reversibly to the EGFR. Erlotinib is indicated as treatment of advanced NSCLC after prior chemotherapy, but is in development for all lines of EGFR mutation positive NSCLC. Gefitinib is indicated in all lines of treatment of advanced NSCLC harbouring EGFR mutations in the tumor. Other small molecule inhibitors of EGFR include afatinib, brigatinib, icotinib, and lapatinib. In one embodiment, a small molecule inhibitor can be a pharmaceutically acceptable salt of the above-described small molecule inhibitors.

EGFR is required for proper activation of TRPM6 channel that plays a role in the transport of Mg in the distal convoluted tubule. Inhibition of EGFR leads to increased fractional excretion of magnesium in patients treated with cetuximab (Groenestege et al., J Clin Invest 2007, 117: 2260-2267) and defective renal magnesium reabsorption in patients treated with EGFR antibodies (Tejpar et al., 2007). In addition to causing magnesium deficiency, blockage of EGFR signaling has also been shown to induce cardiac dysfunction and neurogenic inflammation (Weglicki et al., 2012).

The present disclosure is based, in part, on the surprising discovery that undesirable side effects associated with EGFR blocking drugs such as hypomagnesemia, neurogenic inflammation, cardiac dysfunction and skin lesions and skin rashes can be reduced or prevented by administration of a substance P antagonist.

Accordingly, the disclosure provides methods and compositions for treating these conditions in a subject receiving an EGFR blocking drug, wherein the methods and compositions comprise a substance P antagonist such as an NK-1 receptor antagonist.

Routes of Administration of EGFR Blocking Drugs

The route of administration of an EGFR blocking drug will depend upon the nature and/or type of the inhibitor, the subject, and the nature and severity of the disease and the physical condition of the subject. In various embodiments, an EGFR blocking drug can be administered to a patient orally, intravenously, transdermally, subcutaneously, intranasally, intramuscularly, intraocularly, topically, intrathecally and intracerebroventricularly.

In one embodiment, small molecule inhibitors of EGFR are administered orally and antibody inhibitors of EGFR are administered intravenously. For instance, small molecule inhibitors such as erlotinib, gefitinib, afatinib etc. are typically administered orally. Antibody inhibitors, such as cetuximab and panitumumab, are administered intravenously. Oral dosage forms of small molecule inhibitors.

In embodiments where two EGFR blocking drugs are administered, both drugs can be administered orally or intravenously. Alternatively, one drug can be administered intravenously and the other drug can be administered orally.

EGFR blocking drugs may be administered under fasting or fed conditions depending on the nature and the metabolism of the drug.

Ranges of Administration of EGFR Blocking Drugs

The dosage of an EGFR blocking drug will vary depending on the drug (antibody vs. small molecule), the type of disease, the subject, and the severity of the disease, the physical condition of the subject, the therapeutic regimen (e.g., whether a combination therapeutic agent is used), and the selected route of administration.

In one embodiment, a dosage for a small molecule inhibitor of EGFR ranges from about 20 mg to about 300 mg, about 40 mg to about 250 mg, or about 50 mg to about 200 mg, per day. In various embodiments, a small molecule inhibitor of EGFR is administered in an amount of about 20 mg, 40 mg, 80 mg, 100 mg, 150 mg, 200 mg, 250 mg, or 300 mg per day. For instance, the recommended daily dose of erlotinib for NSCLC is 150 mg taken on an empty stomach, i.e., at least one hour before or two hours after the ingestion of food whereas, for pancreatic cancer, the recommended daily dose of erlotinib is 100 mg taken once daily in combination with gemcitabine on an empty stomach. The recommended daily dose of gefitinib is 250 mg once daily with or without food. The recommended daily dose of afatinib is 40 mg once daily on an empty stomach For antibody inhibitors of EGFR, average weekly dose may vary from about 50 to about 500 mg/m$^2$, e.g. 50, 75, 100, 200, 250, 300, 350, 375, 400, 425, 450, 475 and 500 mg/m$^2$. Alternatively, based on the body weight, a single intravenous dose of about 1 to 15 mg/kg, e.g. 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5 or 15 mg of the antibody/kg of the body weight may be administered. Based on a 70 kg adult patient, this results in 70 to 1050 mg range for a single dose.

For example, the recommended dose for cetuximab is 400 mg/m$^2$ as an initial/loading dose in the first week followed by 250 mg/m$^2$ weekly thereafter. The recommended dose for panitumumab is 6 mg/kg every 14 days.

Novel Patient Populations and Methods of Treating/Alleviating/Preventing Hypomagnesemia A normal range for serum magnesium is from 1.8 to 3.5 mg/dL according to FDA's Investigations Operations Manual (IOM) 2015. The terms "hypomagnesemia" or "magnesium deficiency" as used herein refer to serum magnesium levels lower than about 1.8 mg/dL. Hypomagnesemia in the context of cancer patients receiving chemotherapy is discussed in Saif, 2008 (J Support Oncol, vol. 6 (5), 243-248), which is incorporated by reference herein in its entirety. National Cancer Institute's (NCI) Common Toxicity Criteria defines four grades of severity of hypomagnesemia (Saif, 2008) which are as follows:

TABLE 1

Grades of Severity of Hypomagnesemia: National Cancer Institute-Common Toxicity Criteria Version 3

| Grade 0 | Within normal limits |
|---|---|
| Grade 1 | < LLN-1.2 mg/dL or < LLN-0.5 mmol/L |
| Grade 2 | <1.2-0.9 mg/dL or <0.5-0.4 mmol/L |

TABLE 1-continued

Grades of Severity of Hypomagnesemia: National Cancer Institute-Common Toxicity Criteria Version 3

| Grade 3 | <0.9-0.7 mg/dL or <0.4-0.3 mmol/L |
|---|---|
| Grade 4 | <0.7 mg/dL or <0.3 mmol/L |

Abbreviation:
LLN = lower limit of normal

According to Saif, Mg supplementation is suggested for patients with grade 2 or higher hypomagnesemia. Parenteral administration of Mg is preferred over oral administration as oral Mg supplementation is often poorly tolerated due to diarrhea (Saif, 2008). However, parenteral Mg administration is associated with side effects and/or may not be adequate (Saif, 2008).

In a recent study, Vickers et al. (Annals of Oncology, 2013, 24: 953-960) show that cetuximab-treated patients who show hypomagnesemia of grade ≥1 around day 28 of the cetuximab treatment or ≥20% decrease in Mg levels compared to Mg levels prior to the cetuximab treatment (baseline) have poor overall survival. The above study indicates that hypomagnesemia induced by EGFR blocking drugs need to be treated to improve survival rate. As disclosed in Saif, IV supplementation of Mg may not be effective in treating hypomagnesemia. Thus, there is a need for alternative treatments for reducing or preventing hypomagnesemia in patients receiving EGFR blocking drugs.

The present disclosure provides methods for treating or preventing hypomagnesemia in a subject receiving an EGFR blocking drug, by administering to the subject an effective dose of a neurokinin-1 (NK-1) receptor antagonist. In some embodiments, the disclosure provides methods for treating hypomagnesemia in various sub-populations of patients receiving an EGFR blocking drug. For instance, in one embodiment, the subject receiving an EGFR blocking drug is in need of a treatment for hypomagnesemia when the subject has i) a serum Mg level lower than about 1.8 mg/dL, ii) serum Mg level lower than about 1.2 mg/dL, iii) serum Mg level lower than about 0.9 mg/dl, or iv) serum Mg level lower than about 0.7 mg/dL.

In another embodiment, the subject receiving an EGFR blocking drug is in need of a treatment for hypomagnesemia when the subject i) shows severe side effects in response to intravenous (IV) Mg supplementation, ii) has serum Mg level lower than about 1.2 mg/dL even after IV Mg supplementation, or iii) has serum Mg level lower than about 1.2 mg/dL and is intolerant to IV Mg supplementation.

In another embodiment, the subject receiving an EGFR blocking drug is in need of a treatment for hypomagnesemia when the subject's Mg levels fall below any threshold as set forth and defined in the aforementioned Table 1. For example, the subject may be in need of such treatment if they have a Mg level categorized as Grade 4, or as Grade 3, or as Grade 2, or as Grade 1. The exact level of Mg level that will determine whether or not a patient is in need of the treatments described herein, may vary depending upon the person's particular physiological parameters. However, regardless of the exact Mg threshold level, which can be defined in various ways according to the disclosure, the methods taught herein are able to identify a subpopulation of patients that otherwise would suffer negative consequences from the administration of EGFR blocking drugs.

In yet another embodiment, the subject receiving an EGFR blocking drug is in need of a treatment for hypomagnesemia if the subject shows ≥20% reduction in serum Mg levels compared to Mg levels prior to the treatment with the EGFR blocking drug (baseline). In yet another embodiment, the subject receiving an EGFR blocking drug is in need of a treatment for hypomagnesemia if the subject shows ≥25%, ≥30%, ≥35%, ≥40%, ≥45% or ≥50% reduction in serum Mg levels compared to baseline Mg levels. In yet another embodiment, the subject receiving an EGFR blocking drug is in need of a treatment for hypomagnesemia if the subject shows ≥grade 1 hypomagnesemia after about 3 or 4 weeks of treatment with the EGFR blocking drug.

In yet another embodiment, the subject receiving an EGFR blocking drug is in need of a treatment for hypomagnesemia when the subject shows ECOG PS (Eastern Cooperative Oncology Group Performance Status) Grade of 2 or higher.

ECOG Scale of Performance Status describes a patient's level of functioning in terms of their ability to care for themselves, daily activity, and physical ability (walking, working, etc.). The scale was developed by the Eastern Cooperative Oncology Group (ECOG) and published in 1982.

TABLE 2

ECOG Performance Status

| GRADE | ECOG PERFORMANCE STATUS |
|---|---|
| 0 | Fully active, able to carry on all pre-disease performance without restriction |
| 1 | Restricted in physically strenuous activity but ambulatory and able to carry out work of a light or sedentary nature, e.g., light house work, office work |
| 2 | Ambulatory and capable of all selfcare but unable to carry out any work activities; up and about more than 50% of waking hours |
| 3 | Capable of only limited selfcare; confined to bed or chair more than 50% of waking hours |
| 4 | Completely disabled; cannot carry on any selfcare; totally confined to bed or chair |
| 5 | Dead |

The inventors have found that administration of a neurokinin-1 (NK-1) receptor antagonist in subjects receiving an EGFR blocking drug reduces the severity of hypomagnesemia.

NK-1 Receptor Antagonists

In various embodiments, the NK-1 receptor antagonist is a small molecule therapeutic.

In various embodiments, the NK-1 receptor antagonist is selected from the group consisting of aprepitant, fosaprepitant, serlopitant, vestipitant, tradipitant, orvepitant, casopitant, and a pharmaceutically acceptable salt thereof. In one embodiment, the NK-1 receptor antagonist is aprepitant (Emend™) or a pharmaceutically acceptable salt thereof.

An NK-1 receptor antagonist can be administered to patients receiving an antibody inhibitor of EGFR or a small molecule inhibitor of EGFR. In one embodiment, the antibody inhibitor of EGFR is cetuximab or panitumumab. In one embodiment, the small molecule inhibitor is a tyrosine kinase inhibitor (TKI) selected from the group consisting of erlotinib, gefitinib, afatinib, brigatinib, icotinib, lapatinib, and a pharmaceutically acceptable salt thereof. In one embodiment, the EGFR inhibitor is erlotinib or a pharmaceutically acceptable salt thereof. In a further embodiment, the EGFR inhibitor is erlotinib and the NK-1 receptor antagonist is aprepitant (Emend™).

In one embodiment, administration of an NK-1 receptor antagonist in subjects receiving an EGFR blocking drug results in serum Mg levels that are at least about 10%, 15%, 20%, 25%, 30%, 35%, 40%, 45%, or 50% higher compared to serum Mg levels in the absence of the NK-1 receptor antagonist treatment.

In yet another embodiment, administration of an NK-1 receptor antagonist in subjects receiving an EGFR blocking drug improves serum Mg levels by at least about 10%, 15%, 20%, 25%, 30%, 35%, 40%, 45%, or 50% compared to serum Mg levels prior to the NK-1 receptor antagonist treatment.

In one embodiment, administration of an NK-1 receptor antagonist to a subject receiving an EGFR blocking drug prevents serum Mg levels from falling more than at least about 20%, 25%, 30%, 35%, 40%, 45% or 50% compared to serum Mg levels prior to the treatment.

In another embodiment, administration of an NK-1 receptor antagonist to a subject receiving an EGFR blocking drug reduces the severity of hypomagnesemia. For instance, in one embodiment, a subject receiving an EGFR blocking drug may show or may have developed a grade 2 or higher hypomagnesemia; however, administration of an NK-1 receptor antagonist to the subject results in a lower grade hypomagnesemia. In another embodiment, a subject receiving an EGFR blocking drug may show or may have developed serum Mg levels of ≤1.2 mg/dL; however, administration of an NK-1 receptor antagonist to the subject results in serum Mg levels of more than 1.2 mg/dL. In yet another embodiment, a subject receiving an EGFR blocking drug may show or may have developed serum Mg levels of ≤0.9 mg/dL; however, administration of an NK-1 receptor antagonist to the subject results in serum Mg levels of more than 0.9 mg/dL. In yet another embodiment, a subject receiving an EGFR blocking drug may show or may have developed serum Mg levels of ≤0.7 mg/dL; however, administration of an NK-1 receptor antagonist to the subject results in serum Mg levels of more than 0.7 mg/dL.

It is possible that the subject receiving an EGFR blocking drug may be receiving two EGFR blocking drugs. For example, the subject may be receiving cetuximab and erlotinib or other combinations of EGFR drugs. In these embodiments, a higher dose of an NK-1 receptor antagonist, e.g. aprepitant, may be administered to the subject.

In one embodiment, the subject receiving one or more EGFR blocking drugs may be treated with an NK-1 receptor antagonist and intravenous Mg supplementation.

In certain embodiments, patients are screened for hypomagnesemia prior to beginning chemotherapy. If the patient is diagnosed with hypomagnesemia, treatment for hypomagnesemia such as intravenous Mg supplementation and/or administration of an NK-1 receptor antagonist may be started prior to chemotherapy and continued during the chemotherapeutic treatment. Methods for identifying or diagnosing a patient with hypomagnesemia comprise determining serum Mg levels and/or determining ECOG PS grade of the patient. In one embodiment, the patient with serum Mg levels lower than about 1.8 mg/dL is considered to be suffering from hypomagnesemia. In another embodiment, the patient with ECOG PS grade of 2 or higher is considered to be suffering from hypomagnesemia.

In some embodiments, the subject receiving an EGFR blocking drug may also be receiving a second non-EGFR blocking chemotherapeutic agent. For instance, an EGFR blocking drug, erlotinib, is often combined with cisplatin for the treatment of lung cancer. Cisplatin and other chemotherapeutic agents are known to cause hypomagnesemia. Accordingly, the disclosure provides methods for treating hypomagnesemia in subjects receiving an EGFR blocking drug and a second chemotherapeutic agent by administering to the subject an effective dose of an NK-1 receptor antagonist.

Routes of Administration of NK-1 Receptor Antagonists

In aspects, the present methods for treatment of hypomagnesemia require administration of an NK-1 receptor antagonist, or a pharmaceutical composition containing the NK-1 receptor antagonist, to a patient receiving an EGFR blocking drug. In these embodiments, the NK-1 receptor antagonist compound and/or pharmaceutical compositions can be administered orally.

The compound and/or pharmaceutical compositions may be delivered via oral sustained release dosage forms. Oral dosage forms of NK-1 receptor antagonists are known in the art.

The disclosure also encompasses parenteral administration of the NK-1 receptor antagonist and/or pharmaceutical compositions if oral administration is not feasible or is associated with side effects, etc.

The disclosure shows that the development of hypomagnesemia in subjects receiving an EGFR blocking drug may lead to skin lesions and/or skin rashes. Accordingly, the disclosure also encompasses topical delivery of the NK-1 receptor antagonist and/or pharmaceutical compositions to the subject.

It is possible that the subject may receive the NK-1 receptor antagonist and/or pharmaceutical compositions both orally and topically.

The terms "treat", "treating" and "treatment" all refer to reducing the severity and/or frequency of hypomagnesemia, cardiac dysfunction, neurogenic inflammation, oxidative stress and/or skin lesions (including eliminating them entirely) and/or avoiding the occurrence of one or more of these conditions associated with EGFR blockage.

The term "therapeutically effective amount" refers to a sufficient quantity of the compound, in a suitable composition, and in a suitable dosage form to treat the noted disease conditions. The "therapeutically effective amount" will vary depending on the compound, the severity of the condition, and the age, weight, etc., of the patient to be treated.

The term "loading dose" refers to the amount of the compounds or compositions that is often larger than subsequent doses, administered for the purpose of establishing a therapeutic level of the drug. Alternatively, a loading dose refers to one or a series of doses that may be given at the onset of therapy to achieve a target concentration of an active ingredient quickly.

Doses may be taken at any time convenient to the patient. However, to minimize side effects such as dizziness or drowsiness, a daily dose may be taken at bedtime. NK-1 receptor antagonists have been shown to cause drowsiness in human clinical trials. Thus, in one embodiment of the present disclosure, the NK-1 receptor antagonist is administered before the patient goes to bed.

Ranges of Administration of Therapeutic Compounds

A therapeutically effective dose range for the NK-1 receptor antagonist is from about 1 mg to about 200 mg, about 10 mg to about 200 mg, about 20 mg to about 200 mg, about 30 mg to about 200 mg, about 40 mg to about 200 mg, about 50 mg to about 200 mg, about 60 mg to about 200 mg, about 70 mg to about 200 mg, about 80 mg to about 200 mg, about 90 mg to about 200 mg, about 100 mg to about 200 mg, or about 120 mg to about 200 mg. In one embodiment, a suitable therapeutically effective dose range for the NK-1 receptor antagonist is from about 1 mg to about 150 mg per day, from about 20 mg to about 125 mg per day, from about 50 mg to about 100 mg per day, or from about 80 mg to about 125 mg per day.

In one embodiment, an effective dose for the NK-1 receptor antagonist is from about 80 mg to about 125 mg per day.

In another embodiment, an effective dose for the NK-1 receptor antagonist is from about 120 mg to about 200 mg per day.

In aspects, the methods taught herein provide for treating a patient with an NK1 antagonist dose that is 1% higher, 2% higher, 3% higher, 5% higher, 10% higher, 15% higher, 20% higher, 25% higher or up to 50% higher than the dose of NK1 antagonist normally administered.

In one embodiment, an effective dose of the NK-1 receptor antagonist is administered once daily. In another embodiment, an effective dose of the NK-1 receptor antagonist is administered 2 or 3 times a day. In one embodiment, about 80 mg of the NK-1 receptor antagonist is administered once daily to the subject receiving an EGFR blocking drug. In another embodiment, about 120 mg of the NK-1 receptor antagonist is administered once daily to the subject receiving an EGFR blocking drug.

In some embodiments, an effective dose of the NK-1 receptor antagonist is administered 1 week, 2 weeks, 3 weeks, or 4 weeks after the subject receives a first dose of the EGFR blocking drug. In one embodiment, an effective dose of the NK-1 receptor antagonist is administered 1 or 2 weeks after the first dose of the EGFR blocking drug.

If the patient undergoing chemotherapy is diagnosed with hypomagnesemia prior to beginning chemotherapy, an NK-1 receptor antagonist may be administered in such patients prior to concurrently with the first dose of the chemotherapeutic agent. Such patient may also receive an intravenous Mg supplementation prior to and during chemotherapy.

In some embodiments, the NK-1 receptor antagonist is administered according to a dosing schedule. In one embodiment, the dosing schedule comprises administering at least one loading dose, followed by either (i) a second loading dose, or doses, and a maintenance dose (or doses), or (ii) a maintenance dose or doses, without a second loading dose, as determined to be appropriate by one skilled in the art. The schedule for administration of the loading and maintenance doses may be determined based upon the individual requirements of a particular patient.

In one embodiment of the present disclosure, a loading dose is administered about a week after the first dose of the EGFR blocking drug, followed by administration of a therapeutically effective maintenance dose after an appropriate interval, such as after one day. In another embodiment, a loading dose is administered on day 1 (which may be a week or 2 weeks after the first does of the EGFR blocking drug) and the maintenance dose is administered on day 2 and thereafter for the duration of therapy. In yet another embodiment, a loading dose is administered on day 1, a second loading dose on day 2, and the maintenance dose is administered on day 3 and thereafter for the duration of therapy. In yet another embodiment, the maintenance dose is administered once a day, once every other day, once every third day, once every fourth day or once a week.

In one embodiment, the dosing schedule of the NK-1 receptor antagonist comprises administering a loading dose on day 1 and administering a maintenance dose every day for the next 6 days and repeating this schedule every week until required. In another embodiment, the dosing schedule of the NK-1 receptor antagonist comprises administering a loading dose on day 1 and administering a maintenance dose on days 2 and 3 and repeating this schedule every week until required.

The loading dose may be about 1.5 times, 2 times, 3 times, 4 times or 5 times the maintenance dose. In one embodiment, the loading dose is about 125 mg and the maintenance dose is about 80 mg.

It would be understood by one skilled in the art that NK-1 receptor antagonists, their dosages and dosing schedules described above for treating hypomagnesemia can also be used to treat neurogenic inflammation, systemic oxidative stress, cardiac dysfunction, and skin changes induced by EGFR blocking drugs.

Treatment of Neurogenic Inflammation, Oxidative Stress, and Cardiac Dysfunction

The disclosure shows that treatment with an EGFR blocking drug also induces neurogenic inflammation, as indicated by elevated substance P levels and systemic oxidative stress as indicated by increased 8-isoprostane levels. The disclosure further shows that administration of an NK-1 receptor antagonist such as aprepitant reduced or completely prevented neurogenic inflammation and systemic oxidative stress.

Accordingly, in one embodiment, the disclosure provides methods for treating or preventing neurogenic inflammation in a subject receiving an EGFR blocking drug by administering to the subject an effective dose of an NK-1 receptor antagonist.

In another embodiment, the disclosure provides methods for treating or preventing systemic oxidative stress in a subject receiving an EGFR blocking drug by administering to the subject an effective dose of an NK-1 receptor antagonist. The term "oxidative stress" as used herein refers to an imbalance between the body's systemic generation of reactive oxygen species (ROS) and antioxidant defenses. The term also encompasses disturbances in the normal redox state of cells that lead to excessive generation of reactive oxygen species.

The term "neurogenic inflammation" as used herein encompasses neurogenic inflammation of hair follicles, gut, kidney, heart which may lead to oxidative stress and/or peripheral neuropathy. Administration of an NK-1 receptor antagonist reduces or prevents neurogenic inflammation in one or more of the above-noted tissues/organs and may reduce or prevent oxidative stress and/or peripheral neuropathy. Neurogenic inflammation of hair follicles induced by EGFR blocking drugs in cancer patients may lead to hair loss associated with chemotherapeutic treatment. In one embodiment, administration of an NK-1 receptor antagonist such as aprepitant may reduce or prevent hair loss.

The disclosure also shows that treatment with an EGFR blocking drug induces cardiac dysfunction and administration of an NK-1 receptor antagonist such as aprepitant reduces or prevents cardiac dysfunction.

Accordingly, in one embodiment, the disclosure provides methods for treating or preventing cardiac dysfunction in a subject receiving an EGFR blocking drug by administering to the subject an effective dose of an NK-1 receptor antagonist.

The term "cardiac dysfunction" as used herein includes systolic and diastolic dysfunction, cardiac wall thinning, cardiomyopathy, cardiac arrhythmia, etc. In one embodiment, administration of an NK-1 receptor antagonist improves or prevents one or more of these conditions associated with cardiac dysfunction.

Treatment of Skin Reactions

The disclosure shows that administration of an NK-1 receptor antagonist reduces or prevents skin reactions such as formation of lesions, rashes, and/or patches, induced by treatment with an EGFR blocking drug.

Accordingly, in one embodiment, the disclosure provides methods for treating or preventing skin lesions or rashes in a subject receiving an EGFR blocking drug by administering to the subject an effective dose of an NK-1 receptor antagonist.

In one embodiment, skin lesions or rashes are non-itchy, i.e. patients may develop skin lesions and/or rashes without having any itchiness.

Methods for treating skin changes induced by an EGFR blocking drug encompass oral and/or topical administration of an NK-1 receptor antagonist. For instance, in one embodiment, skin changes in the subject may be treated by oral administration of an NK-1 receptor antagonist. In another embodiment, skin changes may be treated by topically applying a pharmaceutical composition comprising an NK-1 receptor antagonist. In yet another embodiment, the subject showing skin changes in response to an EGFR blocking drug may be treated by oral as well as topical delivery of an NK-1 receptor antagonist.

It would be understood by one skilled in the art that NK-1 receptor antagonists, their dosages and dosing schedules described above for treating hypomagnesemia can also be used to treat neurogenic inflammation, systemic oxidative stress, cardiac dysfunction, and skin changes induced by EGFR blocking drugs.

Topical Pharmaceutical Compositions

In further embodiments, the disclosure provides topical pharmaceutical compositions comprising an NK-1 receptor antagonist and one or more pharmaceutically acceptable carriers or excipients. In one embodiment, the topical composition comprises aprepitant or a pharmaceutically acceptable salt thereof as an NK-1 receptor antagonist. However, the disclosure is not limited to topical compositions comprising aprepitant and contemplates the use of other NK-1 receptor antagonists for preparing such compositions. For instance, in one embodiment, topical composition comprises an NK-1 receptor antagonist is selected from the group consisting of aprepitant, fosaprepitant, serlopitant, vestipitant, tradipitant, orvepitant, casopitant and a pharmaceutically acceptable salt thereof.

Topical compositions useful in the present disclosure may be formulated as a solution comprising an emollient. Such compositions preferably contain from about 1% to about 50% of an emollient(s). As used herein, the term "emollient" refers to materials used for the prevention or relief of dryness, as well as for the protection of the skin. A number of suitable emollients are known and may be used in the present disclosure. For example, Sagarin, Cosmetics, Science and Technology, 2nd Edition, Vol. 1, pp. 32-43 (1972) and the International Cosmetic Ingredient Dictionary and Handbook, eds. Wenninger and McEwen, pp. 1656-61, 1626, and 1654-55 (The Cosmetic, Toiletry, and Fragrance Assoc., Washington, D.C., 7th Edition, 1997) (hereinafter "ICI Handbook") contains numerous examples of suitable materials.

A lotion can be made from such a solution. Lotions typically comprise from about 1% to about 20% (e.g., from about 5% to about 10%) of an emollient(s) and from about 50% to about 90% (e.g., from about 60% to about 80%) of water.

Another type of product that may be formulated from a solution is a cream. A cream typically comprises from about 5% to about 50% (e.g., from about 10% to about 20%) of an emollient(s) and from about 45% to about 85% (e.g., from about 50% to about 75%) of water.

Yet another type of product that may be formulated from a solution is an ointment. An ointment may comprise a simple base of animal or vegetable oils or semi-solid hydrocarbons. An ointment may comprise from about 2% to about 10% of an emollient(s) plus from about 0.1% to about 2% of a thickening agent(s). A more complete disclosure of thickening agents or viscosity increasing agents useful herein can be found in Sagarin, Cosmetics, Science and Technology, 2nd Edition, Vol. 1, pp. 72-73 (1972) and the ICI Handbook pp. 1693-1697.

The topical compositions useful in the present disclosure may be formulated as emulsions. If the carrier is an emulsion, from about 1% to about 10% (e.g., from about 2% to about 5%) of the carrier comprises an emulsifier(s). Emulsifiers may be nonionic, anionic or cationic. Suitable emulsifiers are disclosed in, for example, in McCutcheon's Detergents and Emulsifiers, North American Edition, pp. 317-324 (1986), and the ICI Handbook, pp. 1673-1686.

Lotions and creams can be formulated as emulsions. Typically such lotions comprise from 0.5% to about 5% of an emulsifier(s). Such creams would typically comprise from about 1% to about 20% (e.g., from about 5% to about 10%) of an emollient(s); from about 20% to about 80% (e.g., from 30% to about 70%) of water; and from about 1% to about 10% (e.g., from about 2% to about 5%) of an emulsifier(s).

Single emulsion skin care preparations, such as lotions and creams, of the oil-in-water type and water-in-oil type are well known in the cosmetic art and are useful in the present disclosure. Multiphase emulsion compositions, for example the water-in-oil-in-water type, as disclosed in U.S. Pat. Nos. 4,254,105 and 4,960,764, may also be useful in the present disclosure. In general, such single or multiphase emulsions contain water, emollients, and emulsifiers as essential ingredients.

The topical compositions of this disclosure can also be formulated as a gel (e.g., an aqueous, alcohol, alcohol/water, or oil gel using a suitable gelling agent(s)). Suitable gelling agents for aqueous gels include, but are not limited to, natural gums, acrylic acid and acrylate polymers and copolymers, and cellulose derivatives (e.g., hydroxymethyl cellulose and hydroxypropyl cellulose). Suitable gelling agents for oils (such as mineral oil) include, but are not limited to, hydrogenated butylene/ethylene/styrene copolymer and hydrogenated ethylene/propylene/styrene copolymer. Such gels typically comprise between about 0.1% and 5%, by weight, of such gelling agents.

In addition to the above carriers and excipients, other emollients and surface active agents can be incorporated in the emulsions, including glycerol trioleate, acetylated sucrose distearate, sorbitan trioleate, polyoxyethylene (1) monostearate, glycerol monooleate, sucrose distearate, polyethylene glycol (50) monostearate, octylphenoxypoly(ethyleneoxy) ethanol, decaglycerin penta-isostearate, sorbitan sesquioleate, hydroxylated lanolin, lanolin, triglyceryl diisostearate, polyoxyethylene (2) oleyl ether, calcium stearoyl-2-lactylate, methyl glucoside sesquistearate, sorbitan monopalmitate, methoxy polyethylene glycol-22/dodecyl glycol copolymer (Elfacos E200), polyethylene glycol-45/dodecyl glycol copolymer (Elfacos ST9), polyethylene glycol 400 distearate, and lanolin derived sterol extracts, glycol stearate and glycerol stearate; alcohols, such as cetyl alcohol and lanolin alcohol; myristates, such as isopropyl myristate; cetyl palmitate; cholesterol; stearic acid; propylene glycol; glycerine, sorbitol and the like.

This disclosure is further illustrated by the following additional examples that should not be construed as limiting. Those of skill in the art should, in light of the present disclosure, appreciate that many changes can be made to the specific embodiments which are disclosed and still obtain a like or similar result without departing from the spirit and scope of the disclosure.

All patent and non-patent documents referenced throughout this disclosure are incorporated by reference herein in their entirety for all purposes.

EXAMPLES

Example 1

Animal Model and Treatment Protocol

Experiments on animals were conducted in accordance with the principles given in the US Department of Health and Human Services Guide for the Care and Use of Laboratory Animals and were approved by The George Washington University Institutional Animal Care and Use Committee. Male Sprague-Dawley rats (125-150 g) were purchased from Hilltop Lab Animals, Inc. (Scottdale, Pa.). After 1 week of quarantine, all age-matched rats were placed on an ad libitum Mg normal diet (25 mmole magnesium oxide/kg food regarded as 100% recommended daily allowance for rodents) obtained from Harlan-Teklad (Madison, Wis.) containing extracted casein as the diet base supplemented with essential vitamins and nutrients; or the same diet supplemented with erlotinib (OSI Pharmaceuticals, LLC, Northbrook, Ill. 60062, USA) to obtain a starting dose of 10 mg/kg/day, Emend® (as aprepitant, Merck & Co., INC. USA) to obtain a starting dose of 2 mg/kg/day, or both agents at these doses. Individually-housed rats were weighed and food consumption recorded daily to obtain actual drug dosage: time-range average erlotinib dose over 9 weeks was 7.07 mg/kg/day, and time-range average Emend dose over 9 weeks was 1.41 mg/kg/day. Rats had free access to distilled-deionized water, and were on a 12 h light/dark cycle for up to 9 weeks.

Blood Sample Collection/Preparation:

At periodic intervals, blood was collected (~0.5 ml) aseptically from the tail of anaesthetized rats (2% isoflurane, EZ Anesthesia Chamber with nose cone)(13, 14) in sterile microtainer plasma separator tubes containing heparin and the protease inhibitor, aprotinin (Sigma Chemicals, St. Louis Mo.) to yield final blood concentrations of 10.74 units/ml and 0.016 units/ml, respectively. For subsequent samplings, the scab was carefully removed, and the process was repeated. Plasma was obtained after centrifugation (12,000 rpm, 2 min, RT, IDEXX StatSpin VT, Iris International, Inc., Westwood, Mass.). Tail bleed samples were used for assessment of plasma Mg, and substance P levels. Sacrifice blood samples (~8 ml collected in heparin plus aprotinin containing BD vacutainer SST tubes) were taken from anaesthetized, heparinized (0.3-0.4 ml 358 units/ml heparin in 0.9% NaCl, i.p.) rats from either the vena cava or by cardiac puncture, and were centrifuged (3,500 rpm, 10 min, RT). In addition to the above plasma parameters, sacrifice plasma was also assayed for 8-isoprostane levels, and the whole blood samples were processed for neutrophil isolation and assessment of superoxide anion production.

Plasma Magnesium:

Magnesium levels in 1:50 or 1:100 diluted, acidified (nitric acid) plasma samples were determined by atomic absorption flame emission spectroscopy (wavelength=285.2 nm) using an AA-6200 Shimadzu spectrophotometer (Columbia, Md.) as described (13). Values obtained from standard curves were mg/dl, and reported as % of control.

Plasma Substance P Determination:

Plasma SP levels (14,15) were assessed using an ELISA kit from R&D Systems (Minneapolis, Minn.). This is a competitive binding assay in which SP within samples (50 µl of 1:1 diluted plasma) competes with a fixed amount of horseradish-labeled SP for sites on a murine monoclonal antibody. Color development was inversely proportional to SP concentration and absorbance was read at 450 nm with background subtraction at 540 nm. Values represent % changes in plasma SP levels compared to time-paired controls (100%) and were means±SE of 4-6 rats. Overall average (n=9) of control rat plasma SP levels at 3, 5 and 9 weeks was 593.13±15.6 pg/ml.

Plasma Total 8-Isoprostane:

Plasma samples (with 0.005% BHT added) were processed to obtained total 8-isoprostane. Briefly, plasma aliquots (100 ul) were alkalinized in 2N NaOH at 45° C. for 2 hrs to release lipid bound and esterified isoprostanes. The alkalinized aliquots were then neutralized in 2N HCl. The samples could turn milky and thus, require centrifugation at RT for 5 min at 12,000 rpm in a microcentrifuge (Fisher Scientific, Marathon Micro A). The final supernatants were used for the determination of total 8-isoprostane content by an EIA kit (Cayman Chemical, MI) (13, 16).

Neutrophil Basal and Stimulated Superoxide Production:

At sacrifice, whole blood (3 ml) samples were obtained; neutrophils were isolated by a step-gradient centrifugation method (13,16). Superoxide anion production from neutrophils (0.5-0.75×106/ml) with (stimulated) or without (basal) PMA (phorbol myristate acetate, 100 ng/ml) was assayed in a phosphate buffer (pH 7.6) containing 5 mM glucose, 1 mM $CaCl_2$, 1 mM $MgCl_2$, and 75 µM cytochrome c±50 µg SOD. Superoxide generation was estimated as SOD-inhibitable reduction of cytochrome c using the extinction coefficient: $E550=2.1\times10^4 M^{-1} cm^{-1}$.

Cardiac Nitro-Tyrosine Determination in Histochemical Analysis:

Cardiac tissue was rapidly excised, rinsed in saline, embedded in OCT compound, quickly frozen and kept at 80° C. until used. Cryosections, 5 um thick, were stained by an indirect, immunohistochemical staining method (13) using rabbit anti-rat Nitrotyrosine antibody (5 ug/ml; Millipore, Billerica, Mass.) and the Vecta-Stain Elite ABC kit immunoperoxidase system (Vector Laboratories, Burlingame, Calif.). Samples were examined under an Olympus BX60 microscope, and multiple images were taken with a digital camera (Evolution Color MP; Media Cybernetics, Silver Spring, Md.). Briefly, fresh frozen sections were fixed in 10% formaldehyde, washed in PBS, incubated with 0.3% hydrogen peroxide in methanol for 30 min to block endogenous peroxidase, washed in PBS and incubated overnight at 4 C with rabbit anti nitrotyrosine antibody, which was applied on every slide except negative control. ABC kit reagents for horseradish peroxidase and 3-3' diaminebenzidine (DAB) were used to visualize the antigen-antibody reaction product as brown color. The sections were counterstained with hematoxylin, rinsed, dehydrated and cleared in series of ethanol and xylene and coverslipped.

Non-Invasive Echocardiography:

Anesthetized rats were subjected to echocardiography periodically during the treatment regimens using a GE VingMed System Five Echocardiogram System (12, 13, 17, and 18). Heart rate and rectal temperature (35.9-37.5° C.) were monitored constantly during the imaging. Animals were placed on a warming platform with paws taped down to limit any motion during imaging, and a sterile eye lubricant was applied to prevent eye drying during the procedure. Hair over the thorax was removed first with an electric clipper, and then with a depilatory cream (<2 min exposure). Animals were imaged (10 MHz probe) for about 20 minutes at an image depth of 3 cm. This imaging system allows for both cardiac structure and function evaluation in rats. Systolic function, measured as % fractional shortening (% FS) using M-mode imaging, and left ventricular ejection fraction (LVEF), calculated from M-mode measurements, were assessed. Key anatomical parameters (IVSd & s=interventricular septum diameter in diastole and systole; and LVPWd & s=LV posterior wall thickness in diastole or systole) were measured to assess the presence of dilated or hypertrophic cardiomyopathy. Measurements of the aortic and pulmonary artery diameters were used to calculate stroke volumes. Aortic pressure max (AoPmax) was assessed; and spectral Doppler velocities were measured for the pulmonic and aortic outflows to calculate cardiac output (CO), and for the mitral valve inflows to assess ventricular diastolic function (mitral valve E and A wave velocities and the E/A ratio were obtained). After echocardiography, animals were placed in room air until awake, and observed until fully recovered.

Statistics:

Data were reported as the mean±SEM of 4-7 animals per group. Data were checked by F-test for equality of groups' variation, and statistical differences were evaluated by two-tailed Student's t-test. Selected data were analyzed by one-way ANOVA followed by a Tukey's test. Statistical significance was considered at $p<0.05$.

Example 2

Erlotinib Treatment does not Affect Food Consumption and Weight Gain

Erlotinib (starting 10 mg/kg/day, oral) and/or Emend (aprepitant, starting 2 mg/kg/day, oral) were administered to rats in custom-prepared food. Neither ERL nor Emend affected food consumption of the animals compared to controls (FIG. 1B). Erlotinib alone modestly, but non-significantly depressed animal weight gain (−13%, N.S.) over 9 weeks of drug treatment, suggesting that the dose of erlotinib used had only minor systemic toxicity (FIG. 1A). Emend plus erlotinib slightly improved weight gain (−8%); however, no statistically significant differences were found among any of the treatment groups compared to their time-matched controls or between each other. There were no significant differences in food intake noted among experimental groups and control animals (FIG. 1B). Data are means±SEM of 5-7 rats per group.

Example 3

Erlotinib Promotes Hypomagnesemia and Neurogenic Inflammation

Blood was sampled at specified times from rats treated with erlotinib (starting 10 mg/kg/day, oral) and/or Emend (aprepitant, starting 2 mg/kg/day, oral). Plasma was assessed for magnesium by flame emission atomic absorption spectroscopy (FIG. 2A). Data are the means±SEM of 5-7 animals per group. * $p<0.05$,** $p<0.01$ and # $p<0.001$ compared with the time-matched control group; + $p<0.055$ versus erlotinib alone. Plasma SP (FIG. 2B) was assessed by a colorimetric ELISA kit. Values for erlotinib±Emend rats were compared to time-matched controls (100%), and are means±SEM of 4-6 rats per group. * $p<0.05$ and ** $p<0.01$ compared with the time-matched control group; + $p<0.05$ versus erlotinib alone.

Erlotinib caused no significant hypomagnesemia in rats at 1.5 week (−2%); however from weeks 3 to 9, erlotinib induced moderate but progressively significant decreases in circulating Mg levels as follows: −9% at wk 3, −13% at wk 5, −16% at wk 7; at 9 weeks, a more pronounced decrease (−26%, $p<0.001$) was observed (FIG. 2A). To determine if elevated substance P (SP) might occur due to the drug-induced moderate hypomagnesemia, changes in the circulating SP levels were determined. Although not all erlotinib exposure weeks were sampled, increases in SP during week 3 (27.3%, $p<0.05$), week 5 (12.3%, NS), and week 9 (25.4%, $p<0.01$) were detected (FIG. 2B). Interestingly, these increases were almost completely blocked by co-treatment with the clinically used NK-1 receptor blocker, Emend. FIG. 2A also indicates that in the presence of SP receptor blockade, the severity of hypomagnesemia due to erlotinib was attenuated by ~42% at 9 week.

Example 4

Erlotinib and NK-1 Blockade on Neutrophil Activation and Oxidative Stress

Figure 3A:
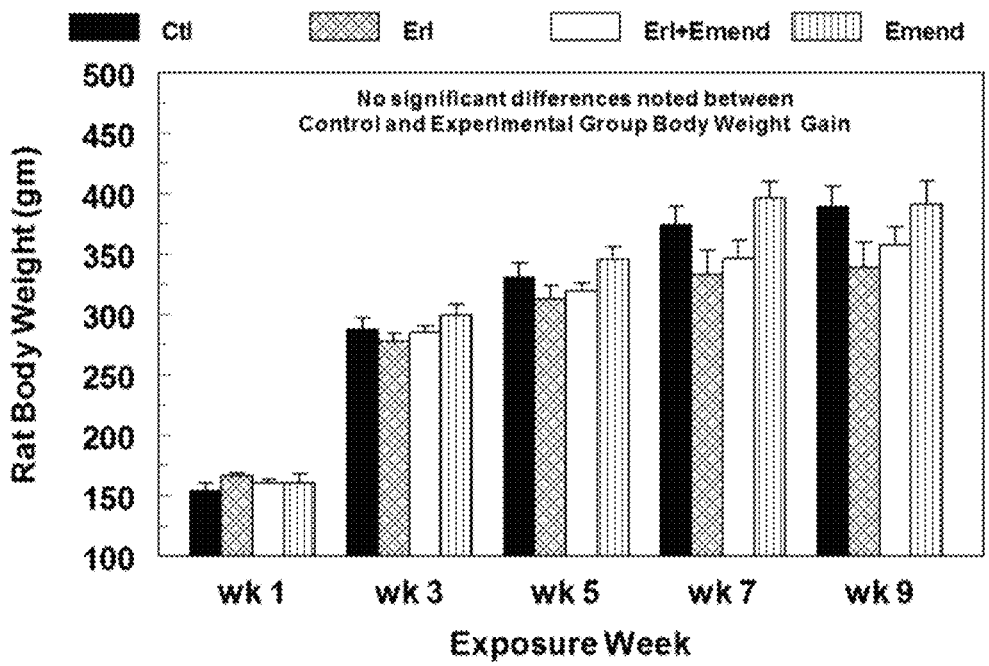
FIG. 3A shows the effect of erlotinib±Emend treatment on the animal weight gain versus control.
Figure 3B:
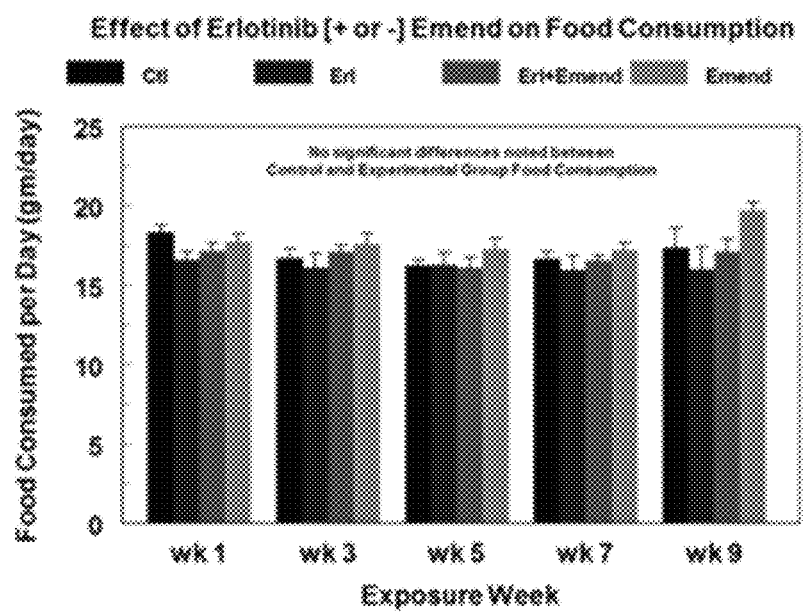
FIG. 3B shows the effect of erlotinib±Emend treatment on the rate of food consumption versus control.

Hypomagnesemia alone in rodents can promote neutrophil free radical generating activity (Mak et al., Exp. & Clin. Cardiol. 2011, 16(4):121-124; Mak et al., Magnesium Res 2003, 16(2):91-97). In the present study, blood was sampled from rats treated with erlotinib (starting 10 mg/kg/day, oral) and/or Emend (aprepitant, starting 2 mg/kg/day, oral) at 9 weeks of exposure. Circulating neutrophil basal superoxide generating activity was determined as SOD-inhibitable reduction of cytochrome c (FIG. 3A). Plasma 8-isoprostane was assessed by a colorimetric ELISA kit (FIG. 3B). Values for erlotinib±Emend rats were compared to time-matched controls, and are means±SEM of 4-6 rats per group. ** $p<0.01$ versus control; ++ $p<0.01$ versus erlotinib alone. Neutrophils isolated from the erlotinib (ERL)-treated rats (9 weeks) displayed a 3-fold higher basal superoxide generating activity (FIG. 3A). When stimulated by PMA, the erlotinib-treated samples also exhibited a 2-fold higher activity compared to controls. Importantly, treatment with Emend completely prevented the increases in both the basal and stimulated superoxide generating activity caused by erlotinib treatment. Enhanced systemic oxidative stress, as represented by increased total plasma 8-isoprostane content (FIG. 3B), was prominent by 9 weeks (210% increase, $p<0.01$). Along with the inhibition of neutrophil activity, Emend completely blocked the elevation of total plasma isoprostane caused by erlotinib. The Emend alone group resembled control values in having no effects on neutrophil superoxide activity or on isoprostane levels.

Example 5

Figure 4A:
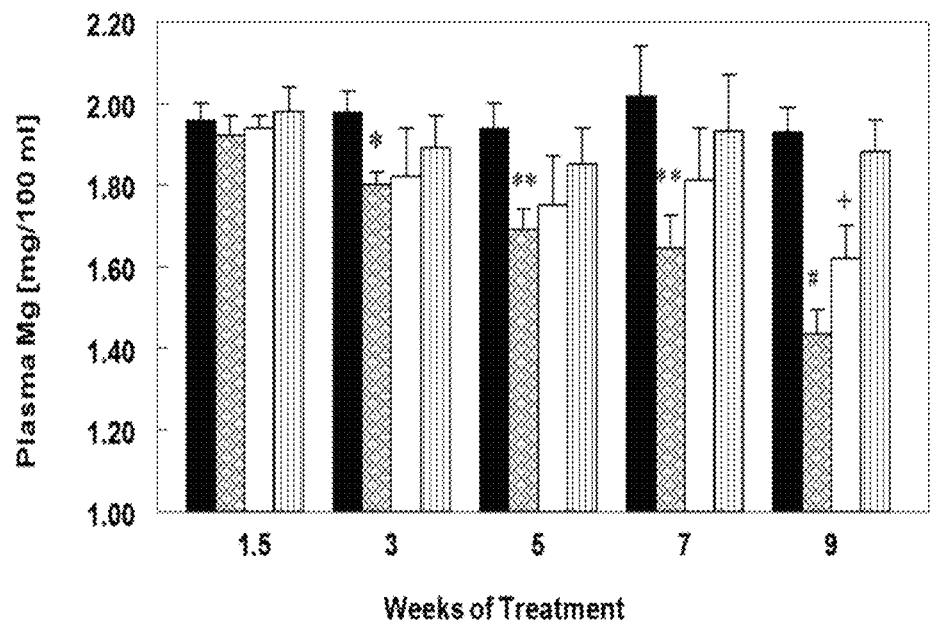
FIG. 4A shows temporal effects of erlotinib with or without Emend treatment for up to 9 weeks on rat plasma magnesium levels.
Figure 4B:
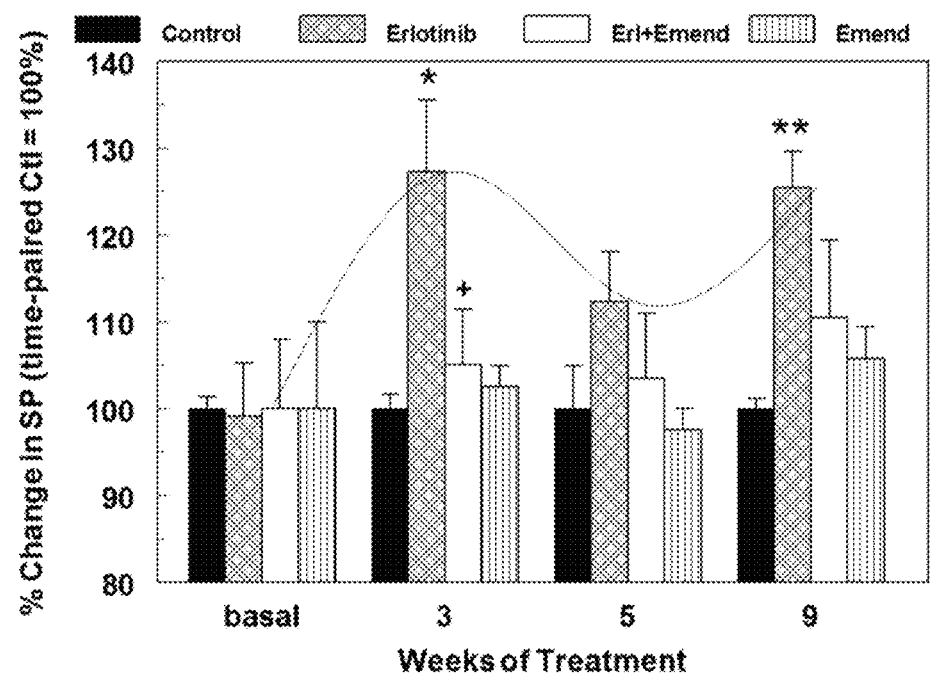
FIG. 4B shows temporal effects of erlotinib with or without Emend treatment for up to 9 weeks on rat substance P levels.

Oxidative Stress Represented by Nitro-Tyrosine (NT) Expression in Cardiac Tissue Immunohistochemical assessment of nitro-tyrosine presence revealed that 9 wk of Erlotinib treatment resulted in substantial perivascular and diffused NT presence, as represented by the enhanced brown staining (FIG. 4). Co-treatment with Emend visibly attenuated nitro-tyrosine formation in the ventricles. Emend treatment alone did not have any effect on nitro-tyrosine formation and the immunohistochemical staining pattern resemble vehicle control samples.

Example 6

Erlotinib and NK-1 Blockade on Cardiac Function

Figure 5A:
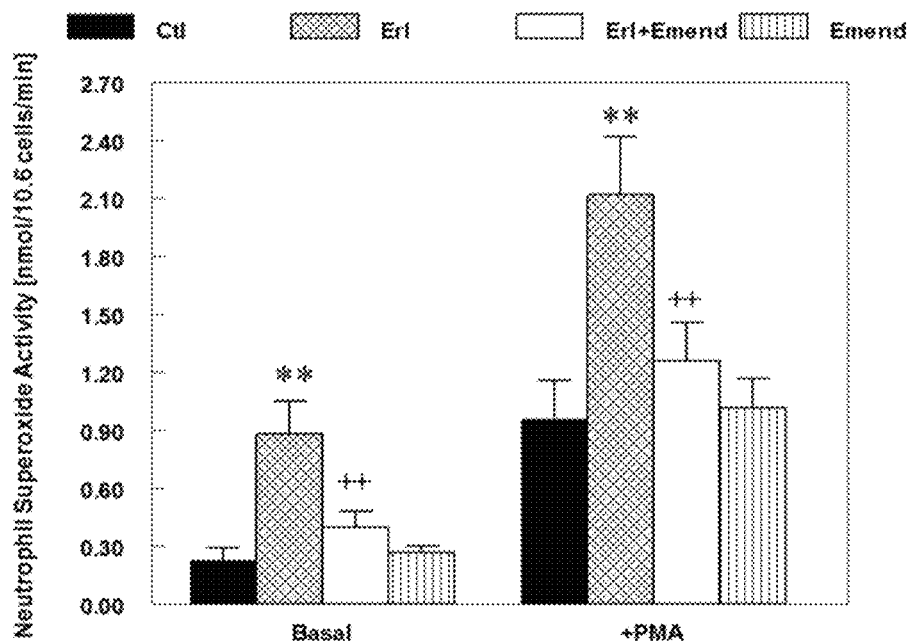
FIG. 5A shows effects of erlotinib with or without Emend treatment for 9 weeks on rat neutrophil basal superoxide generating activity.
Figure 5B:
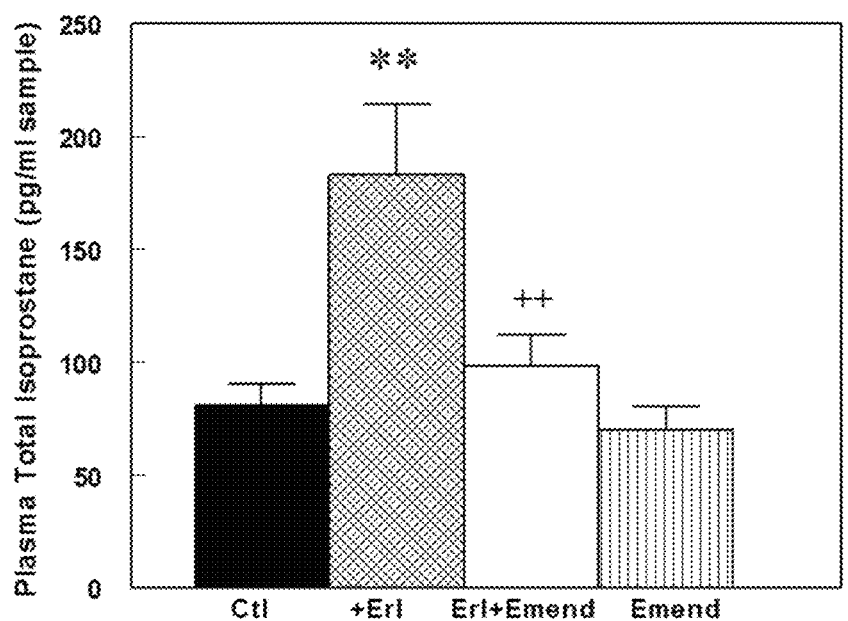
FIG. 5B shows effects of erlotinib with or without Emend treatment for 9 weeks on rat plasma 8-isoprostane content.

Rats treated with erlotinib (starting 10 mg/kg/day, oral) and/or Emend (aprepitant, starting 2 mg/kg/day, oral) received echocardiography at the indicated intervals (FIGS. 5A-5C). Values for erlotinib±Emend rats were compared to time-matched controls (100%), and are means±SEM of 5-7 rats per group. * $p<0.05$ compared with the time-matched control group; $^a$ $p<0.05$ and $^b$ $p<0.02$ versus erlotinib alone.

Figure 6:
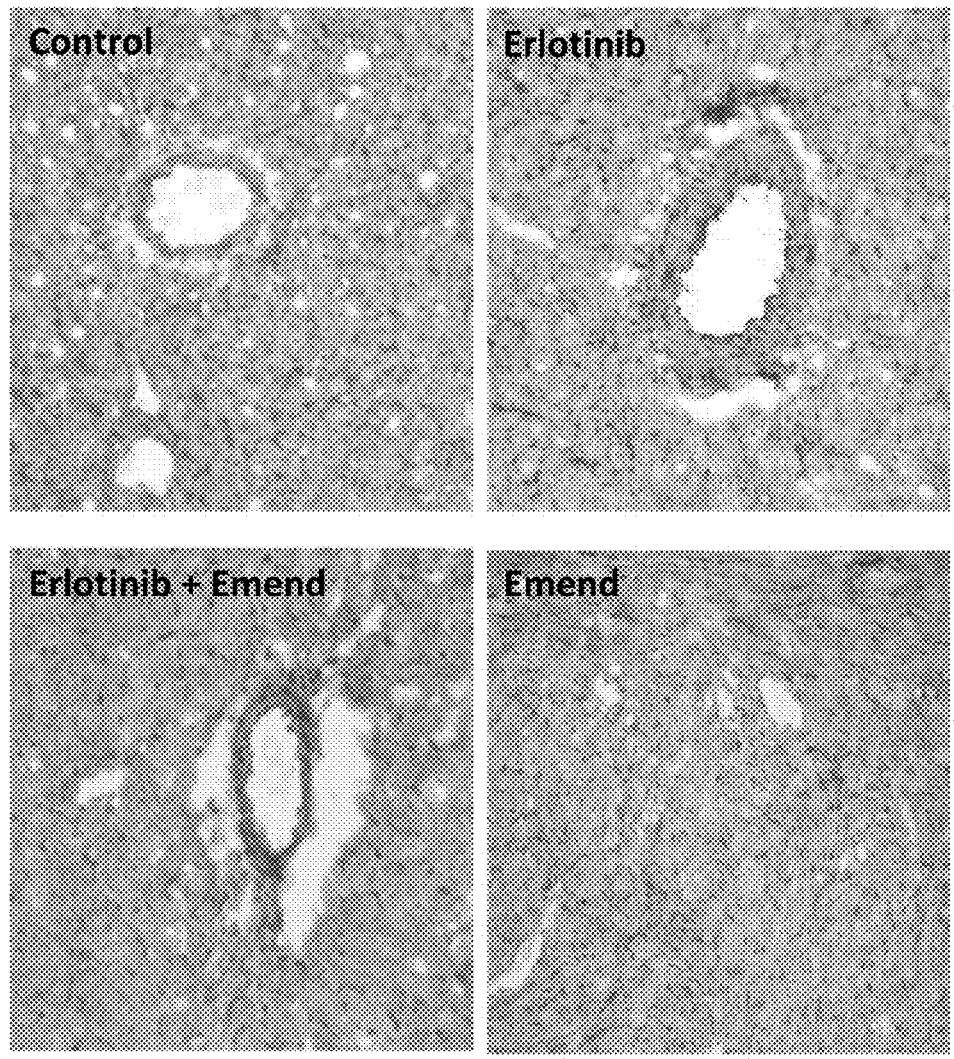
FIG. 6 shows effects of erlotinib with or without Emend treatment for 9 weeks on immunochemical assessment of rat cardiac nitrotyrosine.

No significant changes in cardiac contractile function were detected before 7 weeks in the erlotinib-treated rats; LV ejection fraction (LVEF: left panel, $p<0.05$) was 10.4 and 11% lower and LV % fractional shortening (LV % FS: center, $p<0.05$) was 17.2 and 17.7% lower than time-matched control at 7 and 9 weeks, respectively (FIGS. 5A and 5B). Erlotinib also impaired hemodynamic parameters in a similar exposure time-dependent manner: cardiac output (FIG. 6A) was 18.8 ($p<0.05$) and 20.3 ($p<0.02$) % reduced, and aortic pressure maximum (FIG. 6B) was 17.1 (NS) and 27.5% ($p<0.05$) lower than control at 7 and 9 weeks, respectively. Mitral valve E/A ratio (FIG. 5C) was not significantly affected by erlotinib through 7 weeks, but a significant reduction (17.5%, $p<0.05$) occurred by week 9, suggesting a more delayed development of LV diastolic dysfunction under these treatment conditions. The cardiac anatomical parameters most sensitive to erlotinib exposure were the dimensions of the interventricular septum measured in diastole (IVSd, FIG. 7A) and systole (IVSs, FIG. 7B), and LV posterior wall thickness in diastole (LVPWd, FIG. 8A) or systole (LVPWs, FIG. 8B). Erlotinib caused 12.8 (NS) to 16.8% ($p<0.05$) declines in IVSd during 5 to 9 weeks, and 11.4 to 17.5 (all $p<0.05$) % lower IVSs during this time frame. LVPWd fell 15.6 to 20.9 (all $p<0.05$) % and LVPWs declined 9.3 (NS) to 21.9 ($p<0.05$) % during 5 to 9 weeks of erlotinib exposure (Table 3).

Figures 7A, 7B, 7C:
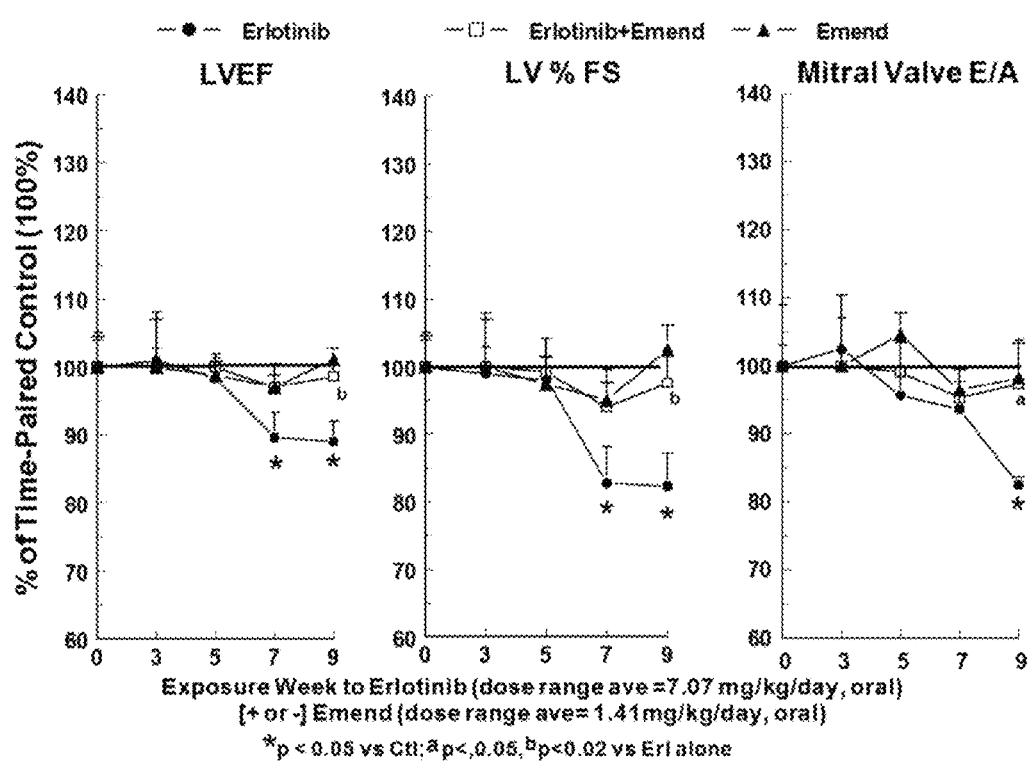
FIGS. 7A-7C show effects of chronic erlotinib±Emend treatment for 9 weeks on echocardiographic functional parameters in rats.
Figures 8A, 8B:
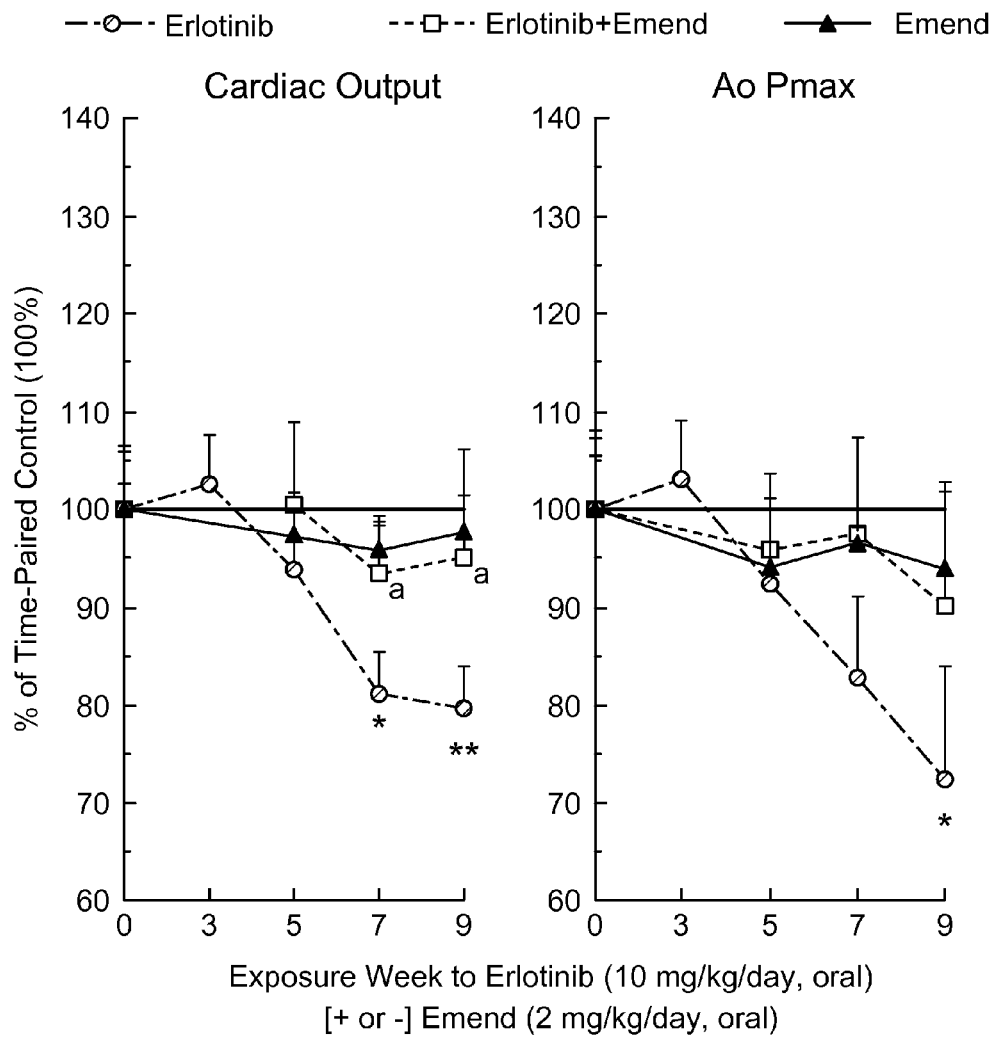
FIGS. 8A-8B show effects of erlotinib±Emend treatment for 9 wks on rat echo parameters.
Figures 9A, 9B:
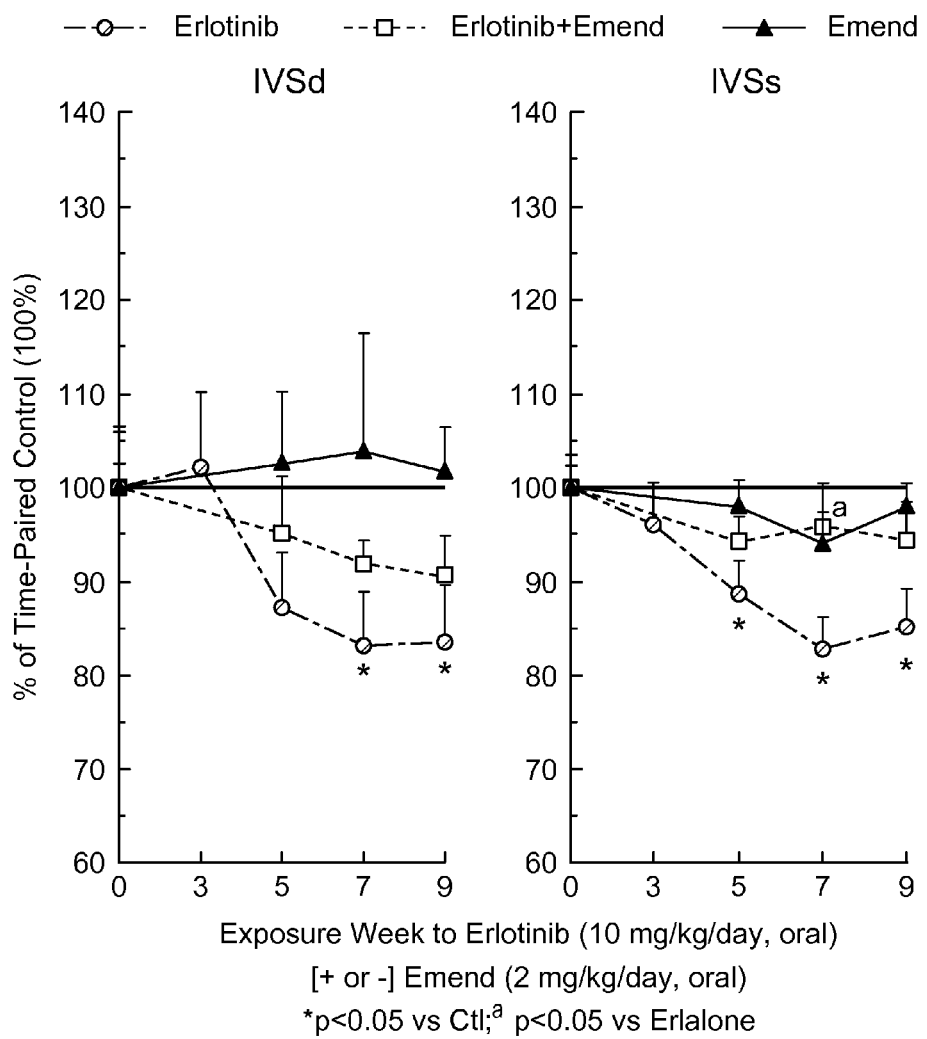
FIGS. 9A-9B show effects of erlotinib±Emend treatment for 9 wks on rat echo anatomical parameters.
Figures 10A, 10B:
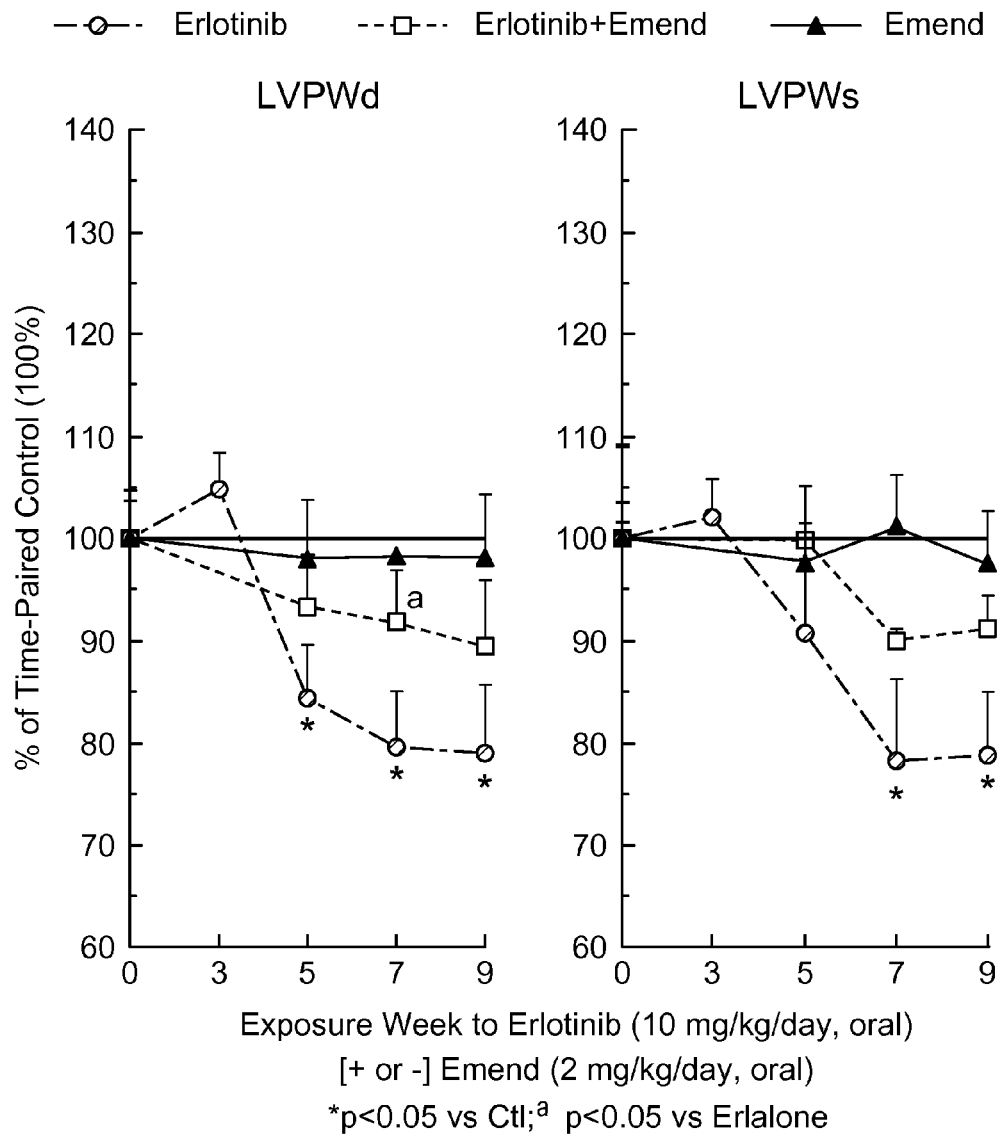
FIGS. 10A-10B show effects of erlotinib±Emend treatment for 9 wks on rat echo anatomical parameters.

Concurrent treatment of erlotinib-exposed rats with Emend attenuated all of the deleterious effects of erlotinib on LV systolic, diastolic and anatomical parameters. Compared to erlotinib alone, Emend co-treatment improved LVEF 71.3% and 87.2% at 7 and 9 ($p<0.02$) weeks (FIG. 5A); improved LV % FS 65.1 and 86.4% at 7 and 9 ($p<0.02$) weeks (FIG. 5B); and improved mitral valve E/A ratio 84.6% at 9 weeks (FIG. 5C, ($p<0.05$)). Emend afforded protection against the erlotinib-induced decline in cardiac output (FIG. 6A) by 64.9 and 75.4% at 7 and 9 weeks ($p<0.02$ vs ERL alone), and also improved AoPmax (FIG. 6B) by 86 (NS) and 64 (NS) % at 7 and 9 weeks. The cardiac anatomical parameters also benefited from Emend co-treatment of erlotinib-exposed rats (Table 3): IVSd improved 48.2 and 42.8% (FIG. 7A); and IVSs improved 76 ($p<0.05$ vs erlotinib alone) and 62% at 7 and 9 weeks (FIG. 7B). LVPWd improved 59.1 ($p<0.05$ vs erlotinib alone) and 49.8% (FIG. 8A); and LVPWs improved 53.4 and 58.2% at 7 and 9 weeks (FIG. 8B). Emend alone did not have any significant impact on LV systolic, diastolic, hemodynamic and anatomical parameters compared to time-paired controls (FIGS. 5-8 and Table 3).

TABLE 3

Changes in rat echocardiography anatomical parameters with drug exposure time

| | Parameter: (±SEM) | | | | | | | |
|---|---|---|---|---|---|---|---|---|
| | IVSd (mm) | % ↓ or ↑ vs Ctl | % ↓ or ↑ vs Ctl | % ↓ or ↑ vs Ctl | IVSs (mm) | % ↓ or ↑ vs Ctl | % ↓ or ↑ vs Ctl | % ↓ or ↑ vs Ctl |
| | | | | | Group: | | | |
| Study Time: | Ctl | Erl | Erl + Emend | Emend | Ctl | Erl | Erl + Emend | Emend |
| 3 weeks | 1.64 ± 0.11 | 2.2%↑ ± 0.17 | nd | nd | 3.14 ± 0.07 | 3.9%↓ ± 0.17 | nd | nd |
| 5 weeks | 1.77 ± 0.09 | 12.82%↓ ± 0.86 | 4.8%↓ ± 0.3 | 2.6%↑ ± 0.19 | 3.22 ± 0.11 | 11.4%↓ ± 0.4 * | 4.62%↓ ± 0.13 | 1.2%↓ ± 0.03 |
| 7 weeks | 1.79 ± 0.06 | 16.8%↓ ± 1.16 * | 8.1%↓ ± 0.21 | 3.95%↑ ± 0.47 | 3.14 ± 0.19 | 17.5%↓ ± 0.7 * | 4.2%↓ ± 0.2 $^a$ | 6%↓ ± 0.21 |
| 9 weeks | 1.91 ± 0.08 | 16.44%↓ ± 1.2 * | 9.4%↓ ± 0.44 | 1.82%↑ ± 0.08 | 3.14 ± 0.07 | 14.4%↓ ± 0.7 * | 5.7%↓ ± 0.25 | 1.94%↓ ± 0.04 |

| | Parameter: (±SEM) | | | | | | | |
|---|---|---|---|---|---|---|---|---|
| | LVPWd (mm) | % ↓ or ↑ vs Ctl | % ↓ or ↑ vs Ctl | % ↓ or ↑ vs Ctl | LVPWs (mm) | % ↓ or ↑ vs Ctl | % ↓ or ↑ vs Ctl | % ↓ or ↑ vs Ctl |
| | | | | | Group: | | | |
| Study Time: | Ctl | Erl | Erl + Emend | Emend | Ctl | Erl | Erl + Emend | Emend |
| 3 weeks | 1.57 ± 0.08 | 4.8%↑ ± 0.16 | nd | nd | 2.306 ± 0.21 | 2%↑ ± 0.07 | nd | nd |
| 5 weeks | 1.77 ± 0.09 | 15.6%↓ ± 0.96 * | 6.7%↓ ± 0.36 | 1.9%↓ ± 0.11 | 2.6225 ± 0.04 | 9.3%↓ ± 0.73 | 0.3%↓ ± 0.01 | 1.7%↓ ± 0.06 |
| 7 weeks | 1.948 ± 0.14 | 20.3%↓ ± 1.11* | 8.3%↓ ± 0.45 $^a$ | 1.7%↓ ± 0.08 | 2.8375 ± 0.09 | 21.9%↓ ± 2.2 * | 10.2%↓ ± 0.14 | 1.2%↑ ± 0.05 |
| 9 weeks | 1.955 ± 0.10 | 20.9%↓ ± 1.74 * | 10.5%↓ ± 0.76 | 1.8%↓ ± 0.11 | 2.9275 ± 0.13 | 21.3%↓ ± 1.7 * | 8.9%↓ ± 0.33 | *2.4%↓ ± 0.12 |

Table 3 legend:
Interventricular septum dimension in diastole (IVSd) and systole (IVSs); and LV posterior wall thickness in diastole (LVPWd) and systole (LVPWs).
Rats treated with erlotinib (starting 10 mg/kg/day, oral) and/or Emend (aprepitant, starting 2 mg/kg/day, oral) received echocardiography at the indicated intervals.
Values (% change) for erlotinib ± Emend rats were compared to time-matched controls, and are means ± SEM of 5-7 rats per group.
Not determined is denoted by nd.
* $p < 0.05$ compared with the time-matched control group;
$^a$ $p < 0.05$ versus erlotinib alone.

Example 7

Emend Blocks Erlotinib-Induced Skin Chances

Male Sprague-Dawley rats (~150 g) were purchased from Hilltop Lab Animals (Scottdale, Pa.). After one week of quarantine, the rats were divided into 4 groups: (1) Control group (N=5) receiving Mg normal diet (25 mmole Mg Oxide/kg food); (2) Erlotinib treated group (N=5, receiving erlotinib at a starting dose of 10 mg/kg/day in the diet); (3) Erlotinib+Emend group (N=7, receiving erlotinib plus Emend at a starting dose of 2 mg/kg/day in the diet); and (4) Emend alone group (N=5). Erlotinib was obtained from OSI Pharmaceuticals, LLC, Northbrook, Ill. and Emend (aprepitant) was obtained from Merck & Co, Inc. After 9 weeks of treatment, the time-range average of erlotinib dose was 7.07 mg/kg/day and the average of Emend was 1.41 mg/kg/day.

After 5 week of treatment prominent skin lesions were observed in Group 2 on the face surrounding the nose area, but such lesions were almost absent in Group 3. No skin changes were observed for group 1 and group 4. At week 9, just before sacrifice, it was noted that all 5 animals of Group 2 developed facial lesion. However, out of the 7 animals in group 3 (Erlotinib+Emend), only 2 had minor levels of lesion develop around the nose area. These studies suggest that Emend protects against Erlotinib-induced skin changes.

INCORPORATION BY REFERENCE

All references, articles, publications, patents, patent publications, and patent applications cited herein are incorporated by reference in their entireties for all purposes.

However, mention of any reference, article, publication, patent, patent publication, and patent application cited herein is not, and should not be taken as, an acknowledgment or any form of suggestion that they constitute valid prior art or form part of the common general knowledge in any country in the world.

REFERENCES

1. Sawyers C. Targeted cancer therapy. Nature 432: 294-297, 2004).
2. Imai K, Takaoka A. Comparing antibody and small-molecule therapies for cancer. Nat Rev Cancer. 2006 September; 6(9):714-27. Review.
3. Schettino C, Bareschino M A, Ricci V, Ciardiello F. Erlotinib: an EGF receptor tyrosine kinase inhibitor in non-small-cell lung cancer treatment. Expert Rev Respir Med. 2008 April; 2(2):167-78. doi: 10.1586/17476348.2.2.167.
4. Tejpar, S., Piessevaux, H., Claes, K., Piront, P., Hoenderop, J. G. J., Verslype, C., and Van Cutsem, E. Magnesium wasting associated with epidermal-growth-factor receptor-targeting antibodies in colorectal cancer: a prospective study. Lancet Oncol. 2007, 8: 387-394.
5. Petrelli F, Borgonovo K, Cabiddu M M D, Ghilardi M, Barni S Risk of anti-EGFR monoclonal antibody-related hypomagnesemia: systematic review and pooled analysis of randomized studies. Expert Opinion on Drug Safety May 2012, Vol. 11, No. 51, Pages S9-S19.
6. Janjigian Y Y, Azzoli C G, Krug L M, Pereira L K, Rizvi N A, Pietanza M C, Kris M G, Ginsberg M S, Pao W, Miller V A, Riely G J. Phase I/II trial of cetuximab and erlotinib in patients with lung adenocarcinoma and acquired resistance to erlotinib. Clin Cancer Res. 2011 Apr. 15; 17(8):2521-7. Epub 2011 Jan. 19.
7. Dimke H, van der Wijst J, Alexander T R, Meijer I M, Mulder G M, van Goor H, Tejpar S, Hoenderop J G, Bindels R J. Effects of the EGFR Inhibitor Erlotinib on Magnesium Handling. J Am Soc Nephrol. 2010 August; 21(8):1309-16. doi: 10.1681/ASN.2009111153. Epub 2010 Jul. 1.
8. Fletcher E V, Love-Homan L, Sobhakumari A, Feddersen C R, Koch A T, Goel A, Simons A L. EGFR inhibition induces proinflammatory cytokines via NOX4 in HNSCC. Mol Cancer Res. 2013 December; 11(12):1574-84. doi: 10.1158/1541-7786.MCR-13-0187. Epub 2013 Sep. 18.
9. Orcutt K P, Parsons A D, Sibenaller Z A, Scarbrough P M, Zhu Y, Sobhakumari A, Wilke W W, Kalen A L, Goswami P, Miller F J Jr, Spitz D R, Simons A L. Erlotinib-mediated inhibition of EGFR signaling induces metabolic oxidative stress through NOX4. Cancer Res. 2011 Jun. 1; 71(11): 3932-40.
10. Yang B, Papoian T. Tyrosine kinase inhibitor (TKI)-induced cardiotoxicity: approaches to narrow the gaps between preclinical safety evaluation and clinical outcome. J Appl Toxicol. 2012 December; 32(12):945-51. doi: 10.1002/jat.2813. Epub 2012 Sep. 10. Review.
11. Doherty K R, Wappel R L, Talbert D R, Trusk P B, Moran D M, Kramer J W, Brown A M, Shell S A, Bacus S. Multi-parameter in vitro toxicity testing of crizotinib, sunitinib, erlotinib, and nilotinib in human cardiomyocytes. Toxicol Appl Pharmacol. 2013 Oct. 1; 272(1):245-55. doi: 10.1016/j.taap.2013.04.027. Epub 2013 May 21.
12. Weglicki, W. B., Kramer, J. H., Spurney, C. F., Chmielinska, J. J., Mak, I. T. The EGFR tyrosine kinase inhibitor tyrphostin AG-1478 causes hypomagnesemia and cardiac dysfunction. Can. J. Physiol. Pharmacol. 2012; 90(8): 1145-9.
13. Mak, I. T, Kramer, J. H., Chen X., Chmielinska, J. J, Spurney, C. F., Weglicki, W. B. Mg-supplementation Attenuates Ritonavir-induced Hyperlipidemia, Oxidative Stress and Cardiac Dysfunction in Rats. Am. J. Physiol. Regul. Integr. Comp. Physiol. 2013; 305: R1102-R1111.
14. Weglicki W B, Chmielinska, J. J., Kramer, J. H., Spurney, C. F., Lu B, Mak, I. T. Neutral endopeptidase inhibition enhances substance P mediated inflammation due to hypomagnesemia. Mag. Res. 2009; 22:1-7.
15. Weglicki, W. B., Mak, I.-T., Chmielinska, J. J., Tejero-Taldo, M. I., Komarov, A., Kramer, J. H. The role of Magnesium Deficiency in Cardiovascular and Intestinal Inflammation. Magnes. Res. 2012; 23(4): S199-206.
16. Mak, I. T., Chmielinska, J. J., Kramer, J. H., Weglicki. W. B. AZT-Induced cardiovascular toxicity—attenuation by Mg-supplementation. Cardiovascular Toxicol. 2009; 9(2):78-85.
17. Kramer, J. H., Spurney, C., Iantorno, M., Tziros, C., Mak, I-T., Tejero-Taldo, M. I., Chmielinska, J. J., Komarov, A. M., Weglicki, W. B. Neurogenic inflammation and cardiac dysfunction due to hypomagnesemia. Am. J. Med. Sci. 2009; 338(1):22-27.
18. Mak I T, Chmielinska J J, Kramer J H, Spurney C F, Weglicki W B. Loss of neutral Endopeptidase activity contributes to neutrophil activation and cardiac dysfunction during chronic hypomagnesemia: Protection by substance P receptor blockade. Exp. & Clin. Cardiol. 2011; 16(4):121-124.
19. Mak I T, Kramer J H, Weglicki W B: Suppression of neutrophil and endothelial activation by substance P receptor blockade in the Mg-deficient rat. Magnesium Res 2003; 16(2):91-97.
20. Van Angelen A A, Glaudemans B, van der Kemp A W, Hoenderop J G, Bindels R J. Cisplatin-induced injury of the renal distal convoluted tubule is associated with hypomagnesaemia in mice. Nephrol Dial Transplant. 2013; 28:879-89.
21. Ledeganck K J, Boulet G A, Bogers J J, Verpooten G A, De Winter B Y. The TRPM6/EGF pathway is downregulated in a rat model of cisplatin nephrotoxicity. PLoS One. 2013; 8(2):e57016. doi: 10.1371/journal.pone.0057016. Epub 2013 Feb. 15.
22. Thebault S, Alexander R T, Tiel Groenestege W M, Hoenderop J G, Bindels R J. EGF increases TRPM6 activity and surface expression. J Am Soc Nephrol. 2009 January; 20(1):78-85. Epub 2008 Dec. 10.
23. Gill P S, Wilcox C S. NADPH oxidases in the kidney. Antiox. Redox Signalling 2006; 8: 1597-1607; 23.
24. Nistala R, Whaley-Connell A, Sowers J R. Redox control of renal function and hypertension. Antioxid Redox Signal. 2008 December; 10(12):2047-89. doi: 10.1089/ars.2008.2034.
25. Cao G, Lee K P, van der Wijst J, de Graaf M, van der Kemp A, Bindels R J, Hoenderop J G. Methionine sulfoxide reductase B1 (MsrB1) recovers TRPM6 channel activity during oxidative stress. J Biol Chem. 2010 Aug. 20; 285(34):26081-7.
26. Weglicki W B, Phillips T M, Pathobiology of magnesium deficiency: A cytokine/neurogenic inflammation hypothesis. Am J Physiol 1992; 263: R734-R737.
27. Weglicki, W. B., Mak, I. T., Kramer, J. H., Dickens, B. F., Cassidy, M. M., Stafford, R. E. and Phillips, T. M. Role of free radicals and substance P in magnesium deficiency. Cardiovasc. Res. 1996; 31:677-682.
28. Kramer, J. H., Mak, I. T., Phillips, T. M. and Weglicki, W. B. Dietary Mg-intake influence circulating pro-inflammatory neuropeptide levels and loss of myocardial tolerance to postischemic stress. Exp. Biol. Med. 2003; 228: 665-673.
29. Ho W Z, Lai J P, Zhu X H, Uvaydova M, Douglas S D. Human monocytes and macrophages express substance P and neurokinin-1 receptor. J Immunol 1997; 159:5654-5660.
30. Dehlin H M, Manteufel E J, Monroe A L, Reimer M H Jr, Levick S P. Substance P acting via the neurokinin-1 receptor regulates adverse myocardial remodeling in a rat model of hypertension. Int J Cardiol. 2013 12; 168(5): 4643-51.
31. Hasinoff, B. B. The cardiotoxicity and myocyte damage caused by small molecule anticancer tyrosine kinase inhibitors is correlated with lack of target specificity. Toxicol. Appl. Pharmacol. 2010; 244(2): 190-195.
32. Hahn V S, Lenihan D J, Ky B. Cancer therapy-induced cardiotoxicity: basic mechanisms and potential cardioprotective therapies. J Am Heart Assoc. 2014 Apr. 22; 3(2): e000665. doi: 10.1161/JAHA.113.000665.
33. Chen M, Kerkelä R, Force T. Mechanisms of cardiac dysfunction associated with tyrosine kinase inhibitor cancer therapeutics. Circulation 2008; 117: 84-95.
34. Metro G, Finocchiaro G, Toschi L, Bartolini S, Magrini E, Cancellieri A, Trisolini R, Castaldini L, Tallini G, Crino L, Cappuzzo F. Epidermal growth factor receptor (EGFR) targeted therapies in non-small cell lung cancer (NSCLC). Rev Recent Clin Trials. 2006 January; 1(1):1-13.
35. Altura, B. T., Wilimzig, C., Trnovec, T., Nyulassy, S., Altura, B. M. Comparative effects of a Mg-enriched diet and different orally administered magnesium oxide preparations on ionized Mg, Mg metabolism and electrolytes in serum of human volunteers. J. Am. Coll. Nutr. 1994; 13(5): 447-454.

36. Barbagallo, M., Belvedere, M., Dominguez, L. J. Magnesium homeostasis and aging. Magnes. Res. 2009; 22(4): 235-246.
37. Garrett C R, Eng C. Cetuximab in the treatment of patients with colorectal cancer. Expert Opin Biol Ther 2011; 11: 937-949.
38. Lockhart A C, Berlin J D. The epidermal growth factor receptor as a target for colorectal cancer therapy. Semin Oncol 2005; 32: 52-60.
39. Groenestege W M, Thebault S, van der Wijst J et al. Impaired basolateral sorting of pro-EGF causes isolated recessive renal hypomagnesemia. J Clin Invest 2007; 117: 2260-2267.
40. Saif M W. Management of hypomagnesemia in cancer patients receiving chemotherapy. J Support Oncol 2008 May-June; 6(5):243-8.
41. Vickers et al. Association of hypomagnesemia with inferior survival in a phase III, randomized study of cetuximab plus best supportive care versus best supportive care alone: NCIC CTG/AGITG CO.17. Ann Oncol. 2013 April; 24(4):953-60.
42. Sagarin, Cosmetics, Science and Technology, 2nd Edition, Vol. 1, pp. 32-43 (1972).
43. International Cosmetic Ingredient Dictionary and Handbook, eds. Wenninger and McEwen, pp. 1656-61, 1626, and 1654-55 (The Cosmetic, Toiletry, and Fragrance Assoc., Washington, D.C., 7th Edition, 1997).
44. McCutcheon's Detergents and Emulsifiers, North American Edition, pp. 317-324 (1986).
45. Mak I T, Kramer J H, Chmielinska J J, Spurney C F, Weglicki W B. EGFR-TKI, erlotinib, causes hypomagnesemia, oxidative stress, and cardiac dysfunction: attenuation by NK-1 receptor blockade. J Cardiovasc Pharmacol. 2015 January; 65(1):54-61.

What is claimed is:

1. A method for treating or preventing hypomagnesemia in a subject receiving an epidermal growth factor receptor (EGFR) blocking drug, comprising:
    administering to the subject an effective dose of a neurokinin-1 (NK-1) receptor antagonist,
    wherein the subject receiving the EGFR blocking drug has a serum magnesium level of 1.2 mg/dl or lower.
2. The method of claim 1, wherein the NK-1 receptor antagonist is selected from the group consisting of: aprepitant, fosaprepitant, serlopitant, vestipitant, tradipitant, orvepitant, and casopitant, or a pharmaceutically acceptable salt of any thereof.
3. The method of claim 1, wherein the NK-1 receptor antagonist is aprepitant.
4. The method of claim 1, wherein the effective dose of the NK-1 receptor antagonist is between about 1 to about 150 mg per day.
5. The method of claim 1, wherein the NK-1 receptor antagonist is administered once daily.
6. The method of claim 1, wherein the NK-1 receptor antagonist is administered according to a schedule, said schedule comprising:
    a) first administering at least one loading dose; and
    b) second administering at least one maintenance dose.
7. The method of claim 6, wherein the loading dose is about 1.5 times, 2 times, 3 times, 4 times, or 5 times the maintenance dose.
8. The method of claim 6, wherein the loading dose is about 125 mg and the maintenance dose is about 80 mg.
9. The method of claim 6, wherein the loading dose is administered on day 1 and the maintenance dose is administered on day 2 and thereafter.
10. The method of claim 1, wherein the NK-1 receptor antagonist is administered a week after the subject receives a first dose of the EGFR blocking drug.
11. The method of claim 1, wherein said EGFR blocking drug is a small molecule inhibitor or an antibody.
12. The method of claim 1, wherein said EGFR blocking drug is a small molecule inhibitor selected from the group consisting of: erlotinib, gefitinib, afatinib, brigatinib, icotinib, and lapatinib, or a pharmaceutically acceptable salt of any thereof.
13. The method of claim 1, wherein said EGFR blocking drug is an antibody selected from cetuximab or panitumumab.
14. The method of claim 1, wherein said EGFR blocking drug is erlotinib.
15. The method of claim 1, wherein said EGFR blocking drug is erlotinib and said NK-1 receptor antagonist is aprepitant.
16. The method of claim 1, wherein the subject receiving the EGFR blocking drug has a Eastern Cooperative Oncology Group Performance Status (ECOG PS) Grade of 2 or higher.
17. The method of claim 1, wherein the subject receiving the EGFR blocking drug has a serum magnesium level of 1.2 mg/dl or lower even after intravenous magnesium treatment.
18. The method of claim 1, wherein said subject is receiving two EGFR blocking drugs, one of the EGFR blocking drugs is an antibody and the second EGFR blocking drug is a small molecule inhibitor.
19. The method of claim 18, wherein said antibody is cetuximab and said small molecule inhibitor is erlotinib.
20. A method for treating or preventing cardiac dysfunction in a subject receiving an epidermal growth factor receptor (EGFR) blocking drug, comprising:
    administering to the subject an effective dose of a neurokinin-1 (NK-1) receptor antagonist,
    wherein the subject receiving the EGFR blocking drug has a serum magnesium level of 1.2 mg/dl or lower.
21. A method for treating or preventing neurogenic inflammation or systemic oxidative stress in a subject receiving an epidermal growth factor receptor (EGFR) blocking drug, comprising:
    administering to the subject an effective dose of a neurokinin-1 (NK-1) receptor antagonist,
    wherein the subject receiving the EGFR blocking drug has a serum magnesium level of 1.2 mg/dl or lower.
22. A method for treating or preventing skin lesions in a subject receiving an epidermal growth factor receptor (EGFR) blocking drug, comprising:
    administering to the subject an effective dose of a neurokinin-1 (NK-1) receptor antagonist,
    wherein the subject receiving the EGFR blocking drug has a serum magnesium level of 1.2 mg/dl or lower.
23. The method of claim 20, wherein said EGFR blocking drug is erlotinib and said NK-1 receptor antagonist is aprepitant.
24. The method of claim 21, wherein said EGFR blocking drug is erlotinib and said NK-1 receptor antagonist is aprepitant.
25. The method of claim 22, wherein said EGFR blocking drug is erlotinib and said NK-1 receptor antagonist is aprepitant.

* * * * *